(12) United States Patent
Aguanno et al.

(10) Patent No.: US 10,513,729 B2
(45) Date of Patent: Dec. 24, 2019

(54) BIOLOGICAL DETECTION SYSTEM AND METHOD OF USE

(71) Applicant: STOKES BIO LIMITED, Limerick (IE)

(72) Inventors: Mauro Aguanno, Singapore (SG); Brian T. Chawke, Limerick (IE); Kieran Curran, Limerick (IE); Tara Dalton, Limerick (IE); Mark Davies, Limerick (IE); Xiaona Hou, Cork (IE); David Kinahan, Kildare (IE); Mark Korenke, Henrico, VA (US); David McGuire, Wexford (IE); Michael Sayers, Kerry (IE); Noel Sirr, Galway (IE); Ryan J. Talbot, Stamford, CT (US); Brian Barrett, Tipperary (IE); Damian Curtin, Kerry (IE); Damien King, Limerick (IE); Conor McCarthy, Cork (IE)

(73) Assignee: STOKES BIO LIMITED, Limerick (IE)

( * ) Notice: Subject to any disclaimer, the term of this patent is extended or adjusted under 35 U.S.C. 154(b) by 710 days.

(21) Appl. No.: 15/055,311

(22) Filed: Feb. 26, 2016

(65) Prior Publication Data

US 2016/0281135 A1    Sep. 29, 2016

Related U.S. Application Data

(63) Continuation of application No. 14/110,635, filed as application No. PCT/US2012/032554 on Apr. 6, 2012, now abandoned.

(Continued)

(51) Int. Cl.
*B01L 3/00* (2006.01)
*C12Q 1/686* (2018.01)
(Continued)

(52) U.S. Cl.
CPC .......... *C12Q 1/686* (2013.01); *B01F 13/0005* (2013.01); *B01F 13/0071* (2013.01);
(Continued)

(58) Field of Classification Search
None
See application file for complete search history.

(56) References Cited

U.S. PATENT DOCUMENTS 7,622,076 B2   11/2009   Davies et al.
8,735,169 B2    5/2014   Davies et al.
(Continued)

FOREIGN PATENT DOCUMENTS

CN    101884941 A     11/2010
WO    2004091763 A2   10/2004
(Continued)

OTHER PUBLICATIONS

International Search Report and Written Opinion issued in Application No. PCT/US2012/032554, dated Sep. 26, 2012.

*Primary Examiner* — Rebecca L Martinez
(74) *Attorney, Agent, or Firm* — Jones Robb, PLLC

(57) ABSTRACT

Provided herein is a biological detection system and method of use wherein the biological detection system comprises at least one mixer or liquid bridge for combining at least two liquid droplets and an error correction system for detecting whether or not proper mixing or combining of the two component droplets have occurred.

18 Claims, 19 Drawing Sheets

Related U.S. Application Data

(60) Provisional application No. 61/473,551, filed on Apr. 8, 2011.

(51) Int. Cl.
  *B01F 13/00* (2006.01)
  *B01F 15/00* (2006.01)
  *G01N 21/64* (2006.01)
  *B01L 7/00* (2006.01)
  *G01N 35/00* (2006.01)

(52) U.S. Cl.
  CPC .. *B01F 15/00214* (2013.01); *B01L 3/502715* (2013.01); *B01L 3/502784* (2013.01); *B01L 7/52* (2013.01); *G01N 21/6428* (2013.01); *G01N 35/00623* (2013.01); *B01L 7/525* (2013.01); *B01L 2200/143* (2013.01); *B01L 2300/06* (2013.01); *B01L 2300/0654* (2013.01); *B01L 2300/0867* (2013.01); *G01N 2021/6439* (2013.01); *G01N 2021/6441* (2013.01); *G01N 2035/00465* (2013.01); *G01N 2201/062* (2013.01)

(56) References Cited

U.S. PATENT DOCUMENTS

| | | |
|---|---|---|
| 8,968,659 B2 | 3/2015 | Davies et al. |
| 9,322,511 B2 | 4/2016 | Davies et al. |
| 9,533,304 B2 | 1/2017 | Davies et al. |
| 9,597,644 B2 | 3/2017 | Davies et al. |
| 9,789,484 B2 | 10/2017 | Chawke et al. |
| 2005/0092681 A1 | 5/2005 | Higashino et al. |
| 2005/0272144 A1 | 12/2005 | Sando et al. |
| 2006/0163385 A1 | 7/2006 | Link et al. |
| 2007/0009411 A1* | 1/2007 | Ray ............... B01D 46/0035 423/210 |
| 2008/0277494 A1 | 11/2008 | Davies et al. |
| 2010/0000304 A1* | 1/2010 | Kim ................. B01L 3/5085 73/64.56 |
| 2010/0015606 A1 | 1/2010 | Davies et al. |
| 2010/0022414 A1* | 1/2010 | Link ............... B01F 3/0807 506/18 |
| 2010/0029512 A1 | 2/2010 | Davies et al. |
| 2010/0109320 A1 | 5/2010 | Davies et al. |
| 2010/0120635 A1 | 5/2010 | Davies et al. |
| 2010/0294048 A1 | 11/2010 | McGuire et al. |
| 2010/0297748 A1 | 11/2010 | Davies et al. |
| 2010/0304443 A1 | 12/2010 | Davies et al. |
| 2014/0111901 A1 | 4/2014 | Chawke et al. |
| 2016/0271606 A1 | 9/2016 | Chawke et al. |

FOREIGN PATENT DOCUMENTS

| | | |
|---|---|---|
| WO | 2007091229 A1 | 8/2007 |
| WO | 2008002882 A2 | 1/2008 |
| WO | 2010009365 A1 | 1/2010 |
| WO | 2012139041 A1 | 10/2012 |

* cited by examiner

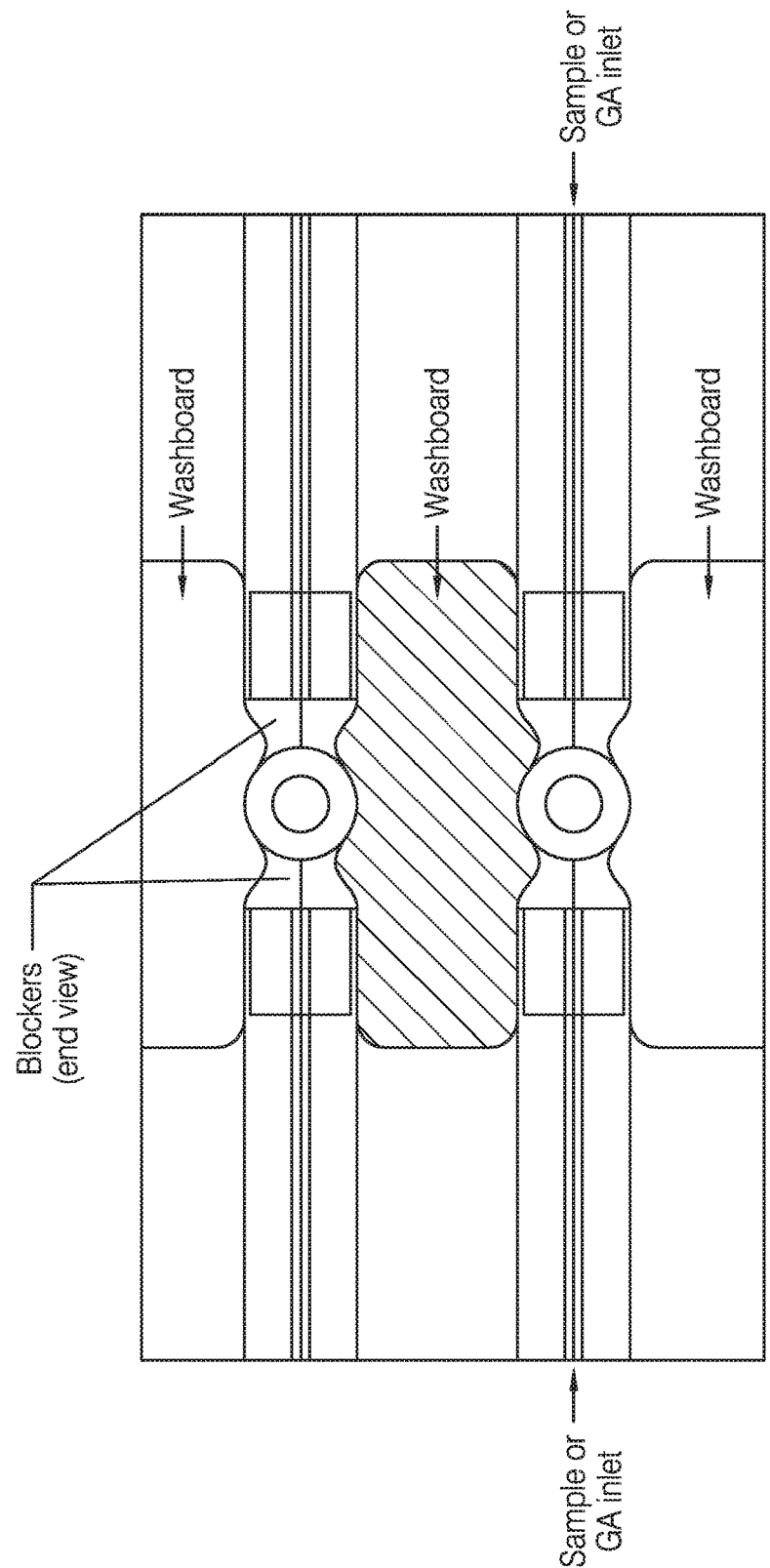

BIOLOGICAL DETECTION SYSTEM AND METHOD OF USE

FIELD OF THE INVENTION

The present invention relates to detection of biological components.

BACKGROUND OF THE INVENTION

Polymerase chain reaction (PCR) systems or thermocyclers typically include a sample block, a heated cover, and heating and cooling elements. These components are then controlled or monitored by an onboard control system. Real-time PCR systems or thermocyclers generally also include an optical detection system for detecting electromagnetic radiation emitted by one or more probes attached to a nucleic acid sample. Real-time PCR systems can additionally include an external computer or control system for controlling and monitoring system components and analyzing data produced by the optical detection system.

Current standard PCR systems and real-time PCR systems are well-based systems. These systems receive samples in a sample support device that includes a plurality of wells. The samples are prepared or mixed with reagents before being loaded into the PCR system. The PCR system then cycles the temperatures of the samples in the wells. Additionally, real-time PCR systems monitor the samples in the wells for electromagnetic or fluorescent emissions.

As the uses and need for genetic and genomic information have increased, so has the need for PCR amplification and analysis. In particular, it has become increasingly important to improve the throughput of PCR systems. Although each generation of PCR systems can cycle the temperatures of samples slightly faster, the technology has not kept up with the performance improvements of other genetic and genomic analysis instruments. For example, deoxyribonucleic acid (DNA) sequencing instruments are advancing to the point where sample preparation and PCR amplification are the most limiting steps in terms of time and cost for sequencing experiments.

In addition, the reliance of current PCR systems on well-based technology limits the overall throughput of these systems. Current systems can cycle the temperatures of samples in approximately 40 minutes. Using the largest well-based sample support device with 384 wells, therefore, produces a maximum overall sample throughput of about 500 samples per hour. Further, current PCR systems receive samples already prepared or mixed in the sample support device. Therefore these systems are dependent on the time consuming and sometimes manual step of well-based sample preparation.

SUMMARY OF THE INVENTION

A system for detecting a biological target comprising a first liquid input for providing a first liquid, a second liquid input for providing a second liquid, at least one mixer in fluid communication with the first liquid input and the second liquid input, wherein the mixer is configured to segment the first liquid into at least one first liquid droplet and the second liquid into at least one second liquid droplet and to create a mixed droplet from the first liquid droplet and the second liquid droplet, and at least one detector, wherein the detector is configured to detect the presence or absence of the at least one first liquid droplet and the at least one second liquid droplet in the mixed droplet. In some embodiments the system may comprise a third liquid input in fluid communication with the mixer wherein the mixer is configured segments the third liquid into at least one third liquid droplet. The system may then mix the first liquid droplet, the second liquid droplet, and the third liquid droplet to form the mixed droplet. Additionally, in some embodiments, the first liquid comprises a first fluorescent dye, the second liquid comprising a second fluorescent dye, and the third liquid comprising a third fluorescent dye, each of the first, second, and third fluorescent dyes emitting fluorescence upon excitation wherein the fluorescence emitted from each is spectrally resolvable from the fluorescence emitted from the others. In some embodiments, the system may include at least one of a thermocycler, an auto sampler, a fluid charging apparatus, such as for example a static bar which may or may not include and electrode.

Further provided herein is a method for detecting proper mixing of at least three liquids, comprising mixing together a first liquid, a second liquid, and a third liquid, each being miscible with the others, to form a mixed sample droplet, the first liquid comprising a first fluorescent dye, the second liquid comprising a second fluorescent dye, and the third liquid comprising a third fluorescent dye, each of the first, second, and third fluorescent dyes emitting fluorescence upon excitation wherein the fluorescence emitted from each is spectrally resolvable from the fluorescence emitted from the others, moving the mixed sample droplet in a conduit, irradiating the mixed sample droplet in the conduit with an excitation source; and detecting emissions from the mixed sample droplet to determine whether each of the first, second, and third fluorescent dyes is present in the mixed sample droplet.

Provided herein is a method for detecting a droplet in system comprising moving the mixed sample droplet in a conduit; irradiating the mixed sample droplet in the conduit with an excitation source; and detecting emissions from the mixed sample droplet to determine whether each of the first, second, and third fluorescent dyes is present in the mixed sample droplet. In some embodiments of the method, the first liquid comprises a first droplet, the first droplet is encompassed by a carrier fluid that is substantially immiscible with the first liquid, the second liquid comprises a second droplet, the second droplet is encompassed by the carrier fluid, the third liquid comprises a third droplet, and the third droplet is encompassed by the carrier fluid. The mixed sample droplet may be encompassed by a carrier fluid that is substantially immiscible with the mixed sample droplet. The mixed sample droplet may be formed at an intersection of the conduit with three other conduits, each of the other conduits containing therein the first liquid, the second liquid, and the third liquid, respectively. The excitation source may include one or more LEDs. The excitation source comprises one or more blue LEDs, each blue LED emitting an excitation beam having a single wavelength that excites each of the first, second, and third fluorescent dyes. The detecting comprises detecting emission from the first fluorescent dye using a first detector, detecting emission from the second fluorescent dye using a second detector, and detecting emission from the third fluorescent dye using a third detector. In some embodiments, the method may further comprise tracking the mixed sample droplet as it moves in the conduit and accepting or rejecting data generated by downstream processing of the mixed sample droplet based on the emissions detected. Additionally, the method may further comprising forming a train of droplets including the mixed sample droplet and detecting emissions from each droplet of the train of droplets. In some embodiments, the method may further comprising forming a train of droplets including the mixed sample droplet, the train of droplets comprising carriages each comprising a plurality of spaced apart droplets, wherein a first spacing is provided between adjacent droplets within each carriage, and the carriages are spaced apart from adjacent carriages by a second spacing that differs from the first spacing. Additionally the methods provided herein may include determining, based on the detected emissions, that proper mixing of the first liquid, second liquid, and third liquid has occurred in the mixed sample droplet; and gathering data from downstream processing of the mixed sample droplet. Alternatively, the method may comprise determining, based on the detected emissions, that improper mixing of the first liquid, second, liquid, and third liquid has occurred in the mixed sample droplet; and recording occurrence of an error; forming a new mixed sample droplet from the first liquid, the second liquid, and the third liquid; and ignoring data generated by downstream processing of the mixed sample droplet. In some embodiments, the first and second dyes comprise a passive reference dye and the third dye comprises a reporter dye.

Further provided herein is a system for detecting proper mixing of at least three liquids, comprising: a conduit system comprising at least a main conduit for carrying a mixed sample droplet; a mixed sample droplet in the main conduit and comprising a first liquid, a second liquid, and a third liquid, the first liquid comprising a first fluorescent dye, the second liquid comprising a second fluorescent dye, and the third liquid comprising a third fluorescent dye, each of the first, second, and third fluorescent dyes emitting fluorescence upon excitation wherein the fluorescence emitted from each is spectrally resolvable from the fluorescence emitted from the others; and an optical detection system comprising an excitation source for irradiating the mixed sample droplet in the main conduit and a detector for detecting emissions from the mixed sample droplet to determine whether each of the first, second, and third fluorescent dyes is present in the mixed sample droplet. The mixed sample droplet may be encompassed by a carrier fluid that is substantially immiscible with the mixed sample droplet. The system of claim 24, wherein the conduit system further comprises a first auxiliary conduit containing therein the first liquid, a second auxiliary conduit containing therein the second liquid, and a third auxiliary conduit containing therein the third liquid; wherein the first, second, and third auxiliary conduits intersect with the main conduit at a junction configured to form the mixed sample droplet. The excitation source may include one or more LEDs or one or more lasers or one or more light sources which may have different wavelengths or the same wavelength. Additionally the detector may include a first detector for detecting emission from the first fluorescent dye, a second detector for detecting emission from the second fluorescent dye, and a third detector for detecting emission from the third fluorescent dye. The first detector, the second detector, and the third detector may each comprise a camera, such as a digital camera or a spectral camera, with or without filters. The system may further comprise a signal processing system for monitoring information generated by the detector and determining whether proper mixing of the first liquid, the second liquid, and the third liquid has occurred in the mixed sample droplet and the first and second dyes comprise a passive reference dye and the third dye comprises a reporter dye. The system may further comprising a train of droplets including the mixed sample droplet, in the main conduit, the train of droplets comprising carriages each comprising a plurality of spaced apart droplets, wherein a first spacing is provided between adjacent droplets within each carriage, and the carriages are spaced apart from adjacent carriages by a second spacing that differs from the first spacing. Additionally, the system may include a conduit support board that holds the main conduit; and an excitation source support board that holds the excitation source; wherein the conduit support board and the excitation source support board are disposed parallel to each other such that the main conduit and the excitation source are aligned with each other and at least a portion of the main conduit is exposed to radiation emitted from the excitation source, where the conduit support board may or may not holds a plurality of main conduits and the excitation source support board holds a plurality of excitation sources. Furthermore, the system may include a plurality of conduit support boards, a plurality of excitation boards, and a housing in which the plurality of conduit support boards and the plurality of excitation support boards are retained. In some embodiments, the system includes a fiber optic cable connected to the detector and configured to receive fluorescent emissions from the main conduit.

Also provided herein is a control unit comprising a processor programmed to carry out a method, the method comprising: mixing together a first liquid, a second liquid, and a third liquid, each being miscible with the others, to form a mixed sample droplet, the first liquid comprising a first fluorescent dye, the second liquid comprising a second fluorescent dye, and the third liquid comprising a third fluorescent dye, each of the first, second, and third fluorescent dyes emitting fluorescence upon excitation wherein the fluorescence emitted from each is spectrally resolvable from the fluorescence emitted from the others; moving the mixed sample droplet in a conduit; irradiating the mixed sample droplet in the conduit with an excitation source; and detecting emissions from the mixed sample droplet to determine whether each of the first, second, and third fluorescent dyes is present in the mixed sample droplet. The processor may be a computer.

Further provided herein is a computer readable medium comprising a program stored thereon, the program comprising a set of instructions for carrying out a method, the method comprising: mixing together a first liquid, a second liquid, and a third liquid, each being miscible with the others, to form a mixed sample droplet, the first liquid comprising a first fluorescent dye, the second liquid comprising a second fluorescent dye, and the third liquid comprising a third fluorescent dye, each of the first, second, and third fluorescent dyes emitting fluorescence upon excitation wherein the fluorescence emitted from each is spectrally resolvable from the fluorescence emitted from the others; moving the mixed sample droplet in a conduit; irradiating the mixed sample droplet in the conduit with an excitation source; and detecting emissions from the mixed sample droplet to determine whether each of the first, second, and third fluorescent dyes is present in the mixed sample droplet.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4a is a bottom view of a ground electrode; FIG. 4b is a side view of the ground electrode shown in FIG. 4a; FIG. 4c is a perspective top view parametric model drawing of the ground electrode shown in FIGS. 4a and 4b;

FIG. 8 is one embodiment of a support structure for a for conduits entering a liquid bridge;

DETAILED DESCRIPTION OF THE INVENTION

Instrument

Figure 1:
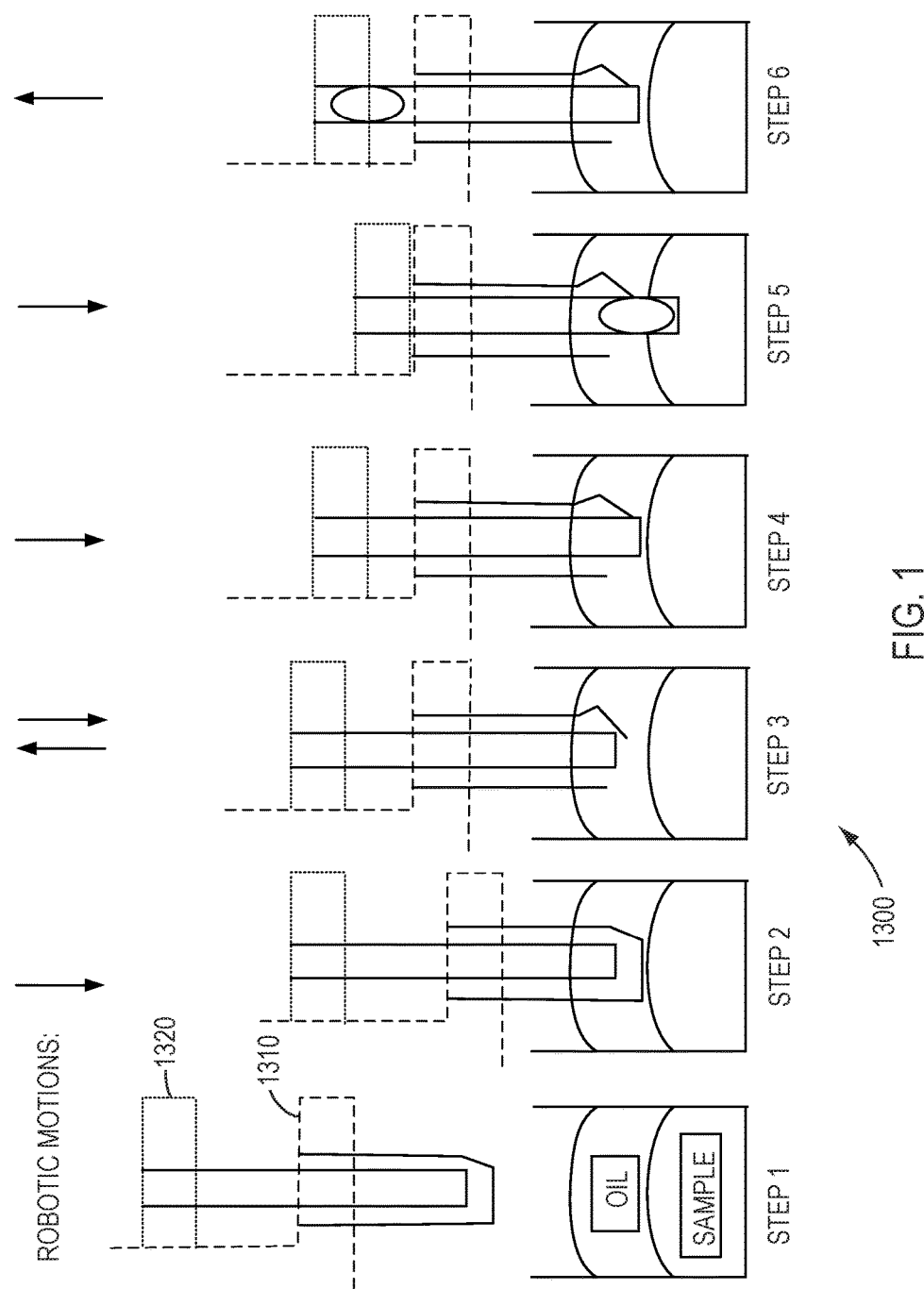
FIG. 1 is a schematic diagram of a flap valve opening method in accordance with various embodiments.

Provided herein is a PCR instrument, in some embodiments a continuous flow 96-line PCR instrument, capable of sampling different fluids or gases from different locations. In some embodiments, the instrument samples the same fluid or different fluids from at least two separate locations. In some embodiments, three different samples may be combined. In some embodiments, the sample may be combined with different fluids such as, for example, a master-mix, a sample and a primer and/or probe simultaneously located separately, and mixing these fluids in a micro-channel geometry, for example in a liquid bridge or other suitable mixer, to form a mixed droplet. The mixed droplet may then flow downstream to a thermocycler where the contents of the droplet may undergo further processing. In some embodiments, the droplet may contain, for example at least one template of a nucleic acid, which may then be subject to conditions for amplification. The droplets and their contents may then pass a data-acquisition system where a parameter of interest may be measured from the droplet such as, for example, concentration or intensity of a dye or multiple dyes located in the droplet, viscosity of the droplet, volume of the droplet, turbidity of the droplet, optical density of the droplet, size of the droplet, or any other suitable parameter.

The instrument provided herein may be comprised from several different individual components, each of which is discussed further herein.

Auto-Sampler

In various embodiments, the system provided for herein may include a fluid sampling device. In some embodiments, the fluid sampling device may be automatic. In some embodiments, the auto-sampling device may be configured to withdraw segmented plugs or droplets of fluid from a fluid vessel. The fluid may be charged fluid or may be a fluid with no charge. The withdrawal and acquisition of fluid may be performed in either a continuous operation or batch operation mode. For example, fluid sampling devices may comprise, for example, the devices described in United States Patent Application Publication Nos. 2010/0304443 and 2010/0294048, which are incorporated by reference in its entirety herein. The devices described in United States Patent Application Publication Nos. 2010/0304443 and 2010/0294048 may be configured to withdraw segmented fluid samples from a vessel, wherein the segmented fluid samples are surrounded by an immiscible carrier fluid.

In some embodiments, the fluid sampling devices may further include at least one robotics system to control the fluid sampling devices. The robotics systems may control movement of the sampling devices to control sample acquisition from the fluid vessel. In some embodiments, the driving force for the withdrawal of charged fluid by a fluid sampling device may be provided by one or more pumps. An exemplary pump is shown in International Patent Application Publication No. WO 2007/091229, which is incorporated by reference in its entirety herein. In some embodiments, the fluid sampling devices may be configured to withdraw fluid using the hydrostatic siphoning effect described in United States Patent Application Publication No. 2010/0120635, which is incorporated by reference in its entirety herein.

In some embodiments, provided herein is a method for generating small volumes of droplets. In some embodiments, droplets of a small volume may be generated using pick-up heads as previously described in United States Patent Application Publication Nos. 2010/0304443 and 2010/0294048, which are incorporated by reference in their entirety. Provided herein is a system that operates under continuous flow such that a first fluid is in continuous contact with the passageway through which the fluid travels such that the first fluid segments a second fluid into discrete volumes and surrounds the second fluids, thereby preventing contact of the second fluid with the passageway. The continuous flow of the system enables collecting a sample located in different wells without drawing air into the system. For example, in some embodiments, a sample is drawn into the system by moving a sample pick-up heads from well-to-well using a continuous flow of a fluid, such as, for example, an oil, such that air is not drawn into the system. In some embodiments the fluid or fluids may be drawn into the system with or without the use of sheathing fluid. In some embodiments, the pick-up heads may include a protective barrier that is configured to prevent air from entering into the system, such as for example, a flap valve. In some embodiments, the protective barrier may be opened and closed using robotic control, pressure, movement, or any other suitable mechanism for opening and closing the protective barrier. In some embodiments, the pick-up heads may draw-up and/or segment a sample fluid using a both sheath fluid and a flap valve. In an embodiment where the sheath tube may be used, the system may comprise a larger bore tube which may be fitted around at least one sampling tube. The sheath tube may provide for a sheath fluid that wraps the at least one sampling tube in oil. The continuous flow of oil into the sheathing tube may match or slightly exceed the flow of the sample being drawn into the system. In such an embodiment, the tips of the sample tubes of the continuous flow lines may be wrapped in oil providing for a continuous flow system. The sheath fluid may be controlled by at least two independent sheathing pumps, and in some embodiments, may be controlled by at least three independently controlled sheathing pumps. Such a system allows the sample pick-up heads to be moved freely from well to well without drawing any air into the system.

FIG. 1 is a schematic diagram of a flap valve opening method 1300, in accordance with various embodiments. In order to facilitate the use of flap valves/sheathing (which needs to be opened before sampling can take place) the tips are mounted on a double Z-axis. The secondary axis 1320 is mounted on the primary axis 1310. The sheathing/flap valves are mounted on primary axis 1310 while the tips are mounted on secondary axis 1320.

In step 1 of method 1300, in air the robotic head moves over the required wells.

In step 2, primary axis 1310 lowers the tips (sheathing and secondary axis 1320) into the oil overlay which covers the sample in each well.

In step 3, secondary axis 1320 then extends the tips (pushing the valves open) so the tip is over the sample. Simultaneously primary axis 1310 rises by an equal distance. The combined effect is that secondary axis 1320 is stationary in space while primary axis 1310 moves upwards. Combined with the geometry of the flap-valves, this movement allows an extra 30 µl volume of sample be used in each (96-wellplate) well.

In step 4, secondary axis 1320 lowers further into the well and completes opening of the flap valve. The secondary axis 1320 pauses until triggered to sample.

In step 5, at the precise time required, secondary axis 1320 dips into the fluid and draws up approximately 75 nl of fluid (sample/primer-probe, master mix approx. 150 nl). The amount of fluid drawn depends on the flow-rate used and the time the tip is within the fluid.

In step 6, the tip then retracts from the sample and pauses ready to sample again if required. If the next sample is needed from a neighboring well (or a plate-change) the tip retracts into the sheathing and the primary axis 1310 then moves the sampling head out into the air. The sheathing motion is a reverse of the unsheathing motions.

Figure 2:
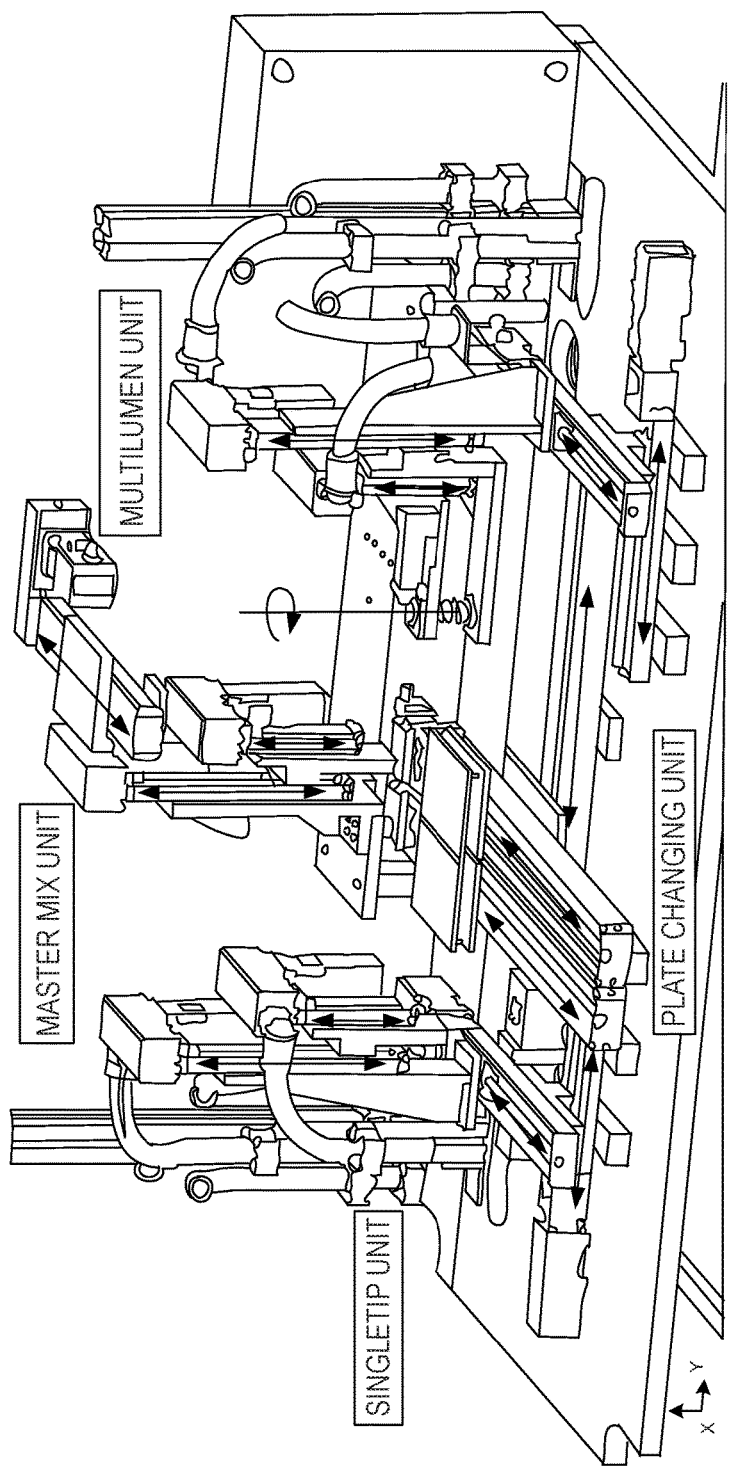
FIG. 2 is a schematic diagram of a liquid/plate handling system in accordance with various embodiments.

FIG. 2 is a schematic diagram of a liquid/plate handling system 1400, in accordance with various embodiments. In system 1400, the liquid/plate handling provides movement along 15 axes. For reference, system 1400 is divided into three sampling systems and one plate handling system. The directions of motion of each stage are shown by arrows. Note that the sampling arm of the multi-lumen unit is shown. However, for clarity, the sampling arms of the master-mix unit and single-tip unit are rendered invisible. Additionally the master mix unit is mounted on the roof of the enclosure. The individual axes are:

Single-Tip Sampling
X-axis
Y-axis
Primary Z-axis (Z1)
Secondary Z-axis (Z2)
Multi-Lumen Sampling
X-axis
Y-axis
Primary Z-axis (Z1)
Secondary Z-axis (Z2)
Rotational Axis
Master-Mix Sampling
X-axis
Primary Z-axis (Z1)
Secondary Z-axis (Z2)
Plate Handling
Y-axis
X1-axis (Tray1-Single-tip)
X2-axis (Tray2-Multi-lumen)

The single-tip system consists of 96 tips each of which can enter a single well on a 96-well or 384-well plate. Therefore system 1400 can sample from a 96-well plate in a single movement or a 384-well plate in four movements. The multi-lumen system consists of four bundles of 24-tips. All 24 lines in each bundle can enter a single well. Each line in the bundle is arrayed against one of the single-tip lines—meeting in a bridge. In some embodiments, the liquid bridge line flows directly into the thermocycler. In some embodiments, the output from a liquid bridge may be captured into a containment unit and then further processed in the container unit or withdrawn from the containment unit for further processing. The multi-lumen head is mounted on a rotational unit. Therefore through four rotations and dips, four wells on Tray 2 (Multi-lumen side) may be arrayed against an entire 96-well plate. Similarly 16 robotic movements (four multi-lumen rotations times four single-tip movements) can permit four wells on Tray 2 be arrayed against an entire 384-well plate.

When exposing the tip of a sampling device to different samples carry-over between tips may occur. In some embodiments over Sample carryover/contamination may occur when the sampling tubes are exposed to concentrated samples. Sample contamination may be reduced by minimizing the area of the sampling tube exposed to the sample. The area of the sampling tube exposed to the sample may be minimized in various ways. In some embodiments, a reduced portion of a sampling tube may extend from a sheath tube. Such a tube in tube embodiment may be fabricated by inserting at least a portion of the sampling tube in a sheath tube. In some embodiments, the sampling tube may be etched on the exterior surface. The sampling tube may then be placed inside a sheath tube. In some embodiments, the interior surface of the sheath tube may be etched as well. Placing the sampling tube in the sheath tube may create at least a partial seal which prevents the exterior surface of the sampling tube from being contaminated. In some embodiments, friction between the inner tube and outer tube causes a seal between the two tubes. In some embodiments, an adhesive may be used to form a seal between the sampling tube and sheath tube. Examples of adhesives that may be used include, for example, glue, epoxy, putty, or any other suitable adhesive. Once a partial seal has been formed between the sampling tube and sheath tube, the combined tube may be cut to expose the distal end of the sampling tube. In some embodiments, the combined tube may be laser cut to ensure a smooth finish on the distal end of the tip. Creating a nested sampling tube structure may lead to a reduction in the cross-sectional area of the wall of up to 92%.

Static Charging of Droplets

In various embodiments, a fluid charging system configured to charge a fluid contained in a fluid vessel comprises an ionizing electrode and a ground electrode. The ionizing electrode and the ground electrode may be positioned adjacent to the fluid vessel. The ionizing electrode and the ground electrode may be opposed so that the fluid vessel is positioned between the ionizing electrode and the ground electrode. The ionizing electrode and the ground electrode are configured to produce an ion field that contacts fluid contained in the fluid vessel, thereby charging the fluid. Various embodiments of static charging systems are described in U.S. application Ser. No. 61/473,317, entitled "System and Method for Charging Fluids", which is incorporated by reference in its entirety.

In various embodiments, a method for charging a fluid contained in a vessel comprises producing an ion field between an ionizing electrode and a ground electrode. A fluid-containing vessel may be positioned adjacent to and between the ionizing electrode and the ground electrode. The ion field produced by the ionizing electrode and the ground electrode contacts the fluid contained in the fluid vessel, thereby charging the fluid. The devices, systems, and methods disclosed herein may be used to produce a net charge in various fluids.

Fluid charged in the devices, systems, and methods disclosed herein may be mixed with other fluids after being charged. The net charge carried by the fluids charged in the devices, systems, and methods disclosed herein may increase the extent of the mixing of fluids in downstream devices, systems, and methods. For instance, fluids carrying a net charge may exhibit improved mixing with other miscible fluids when mixed with fluid plugs or droplets in an immiscible carrier fluid in microfluidic system. In this manner, the net charge may decrease undesirable static electric effects observed in microfluidic systems that can adversely affect fluid mixing.

In various embodiments, a fluid charging system may comprise one or more fluid sampling devices configured to withdraw charged fluid from the fluid vessel, such as described and illustrated below. In various embodiments, the fluid sampling devices may comprise one or more tubes, such as, for example, capillary tubes, configured to withdraw charged fluid from the fluid vessel. In various embodiments, the fluid sampling devices may comprise one or more sheaths, wherein each sheath surrounds one or more tubes, such as, for example, capillary tubes, configured to withdraw charged fluid from the fluid vessel. In various embodiments, the one or more fluid sampling devices may be in continuous or discontinuous fluid communication with the fluid vessel.

Fluid charging systems including fluid sampling devices may further include at least one robotics system to control the fluid sampling devices. The robotics systems may control movement of the sampling devices to control sample acquisition from the fluid vessel. In various embodiments, the driving force for the withdrawal of charged fluid by a fluid sampling device may be provided by one or more pumps. An exemplary pump is shown in International Patent Application Publication No. WO 2007/091229, which is incorporated by reference herein. In various embodiments, the fluid sampling devices may be configured to withdraw fluid using the hydrostatic siphoning effect described in United States Patent Application Publication No. 2010/0120635, which is incorporated by reference herein.

In various embodiments, the ionizing electrode may comprise an emitter plate and one or more emitter pins connected to the emitter plate. The emitter plate may be made of a conductive metallic material, such as, for example, a stainless steel alloy. The emitter pins may be made of a metallic or ceramic material comprising tungsten. For instance, the emitter pins may comprise tungsten carbide, such as, for example, emitter pins made of tungsten carbide or a cemented tungsten carbide (cement) composite material. Alternatively, the emitter pins may be made of a metal alloy comprising tungsten, for example.

In operation, electrical current delivered to the ionizing electrode concentrates at the tips of the emitter pins and ionizes atoms and/or molecules comprising the surrounding air or other gaseous atmosphere, producing an ion cloud. The ion cloud emits from the emitter pins and moves toward the ground electrode along a static electric field established between the ionizing electrode and the ground electrode in accordance with the physical principles of static electricity. This produces an ion field between the ionizing electrode and the ground electrode. The polarity of the ion field is the same as the polarity of the electrical current provided to the ionizing electrode. Although the ion fields illustrated in the figures presented herein are shown with a positive polarity (+) symbol, it is understood that, in various embodiments, the ion field may be of negative polarity. Materials contacting the ion field become charged at the same polarity as the ion field.

Figure 3:
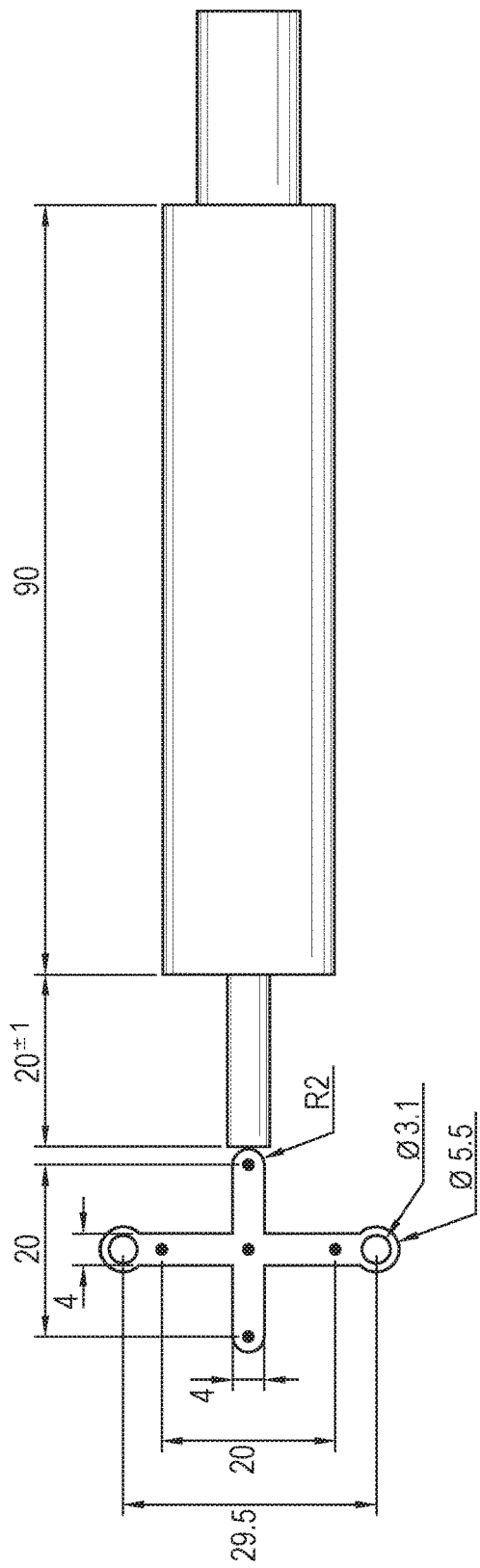
FIG. 3 is a bottom view parametric model drawing of an ionizing electrode assembly.
Figures 4A, 4B, 4C:
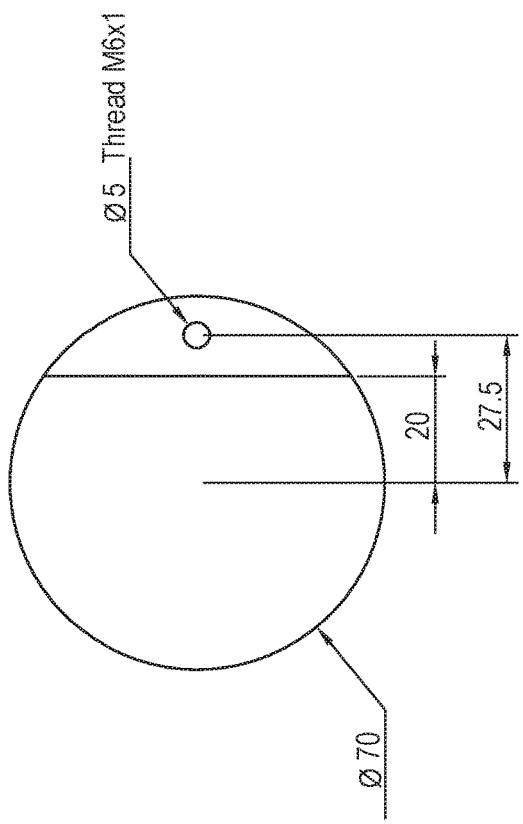

A fluid charging system is provided for charging fluids to be mixed with other fluids in a microfluidic system. The system includes a Fraser Model 7330 static generator connected to an ionizing electrode assembly via a high voltage cable. The ionizing electrode assembly includes a cross-shaped electrode comprising a cross-shaped stainless steel emitter plate and five (5) tungsten emitter pins. The ionizing electrode is connected to a 100 megaohm resistor unit via a high voltage lead. The ionizing electrode assembly has the dimensions and configuration shown in FIG. 3 (dimensions in millimeters). A ground electrode comprises a circular aluminum static ground plate that sits in a non-conductive acrylic holder. The ground electrode has the dimensions and configuration shown in FIGS. 4a, 4b, and 4c (dimensions in millimeters). The ground electrode is connected to the ground lug on the static generator.

In various embodiments, a fluid vessel may be positioned between and adjacent to the electrodes so that the ion field contacts fluid contained within the fluid vessel, thereby charging the fluid. The emitter pins may be connected to the side of the emitter plate that faces an open top end of a fluid vessel, which facilitates contact between the field produced by the ionizing electrode and fluid contained in the fluid vessel to charge the fluid. Although the ionizing electrodes illustrated in certain figures presented herein are shown positioned adjacent an open top end of a fluid vessel, it is understood that, in various embodiments, the ionizing electrodes may be positioned adjacent to any region or end of an open or closed fluid vessel, provided the ionizing electrodes and ground electrodes are mutually positioned in a spaced apart relationship.

Figure 5:
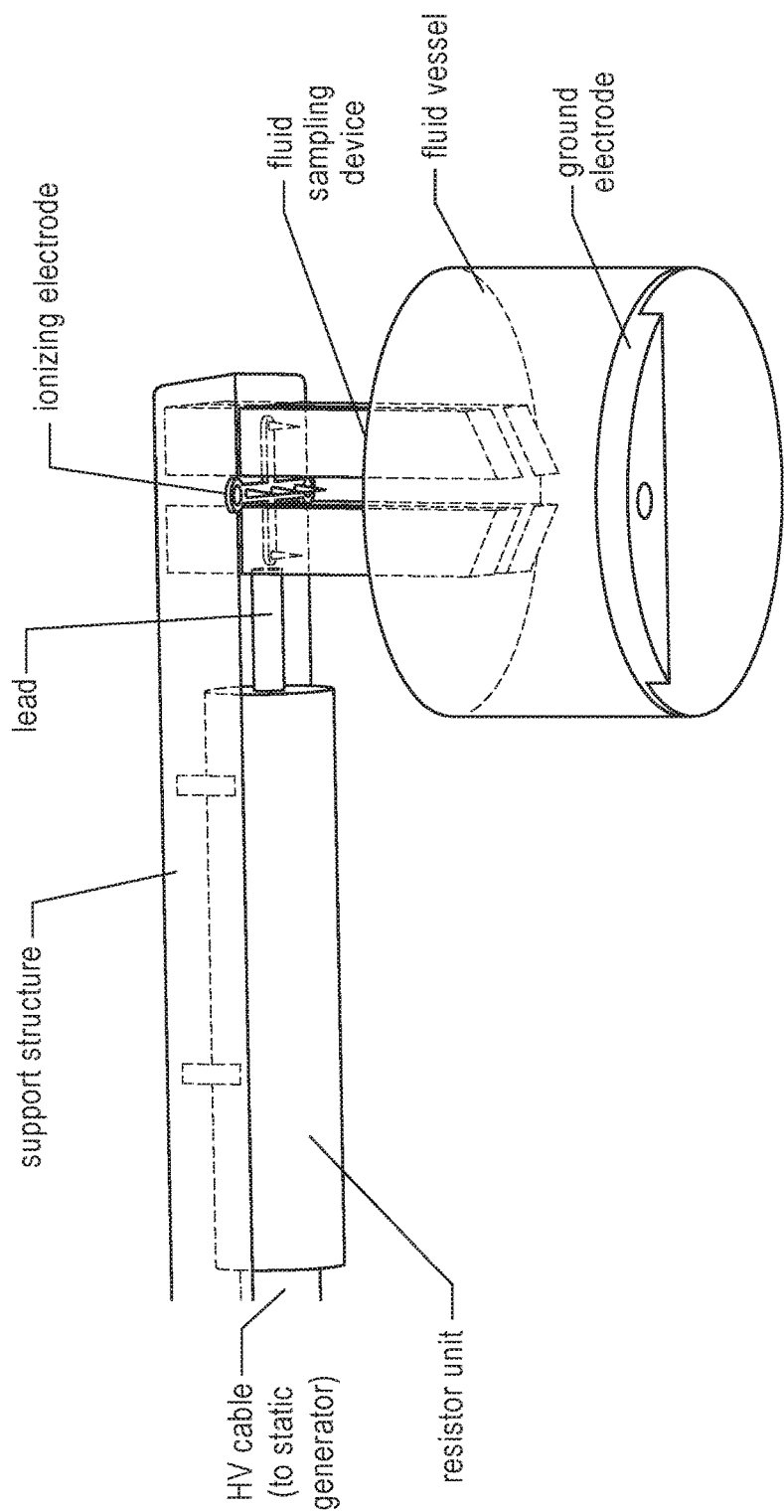
FIG. 5 is a perspective bottom view parametric model drawing of the electrode assembly.

FIG. 5 shows the ionizing electrode and the ground electrode positioned adjacent to a glass fluid vessel. The ionizing electrode and the ground electrode are opposed so that the fluid vessel is positioned between the ionizing electrode and the ground electrode. The glass fluid vessel has an outer diameter that substantially matches the diameter of the ground electrode, the ground electrode and holder being dimensioned to seat and support the fluid vessel. Four (4) fluid sampling devices are positioned through open quadrant regions of the emitter plate of the ionizing electrode. The four (4) fluid sampling devices include sheaths surrounding tubes configured to withdraw fluid from the fluid vessel.

In various embodiments, a fluid sampling device may be in fluid communication with a fluid dispensing device configured to dispense charged and/or mixed fluids to vessels, such as, for example, eppendorf tubes, vials, beakers, flasks, centrifuge tubes, capillary tubes, cryogenic vials, bags, channels, cups, containers, microtiter plates, microcards, and the like. The transport of charged fluids from the fluid vessel to other vessels may be accomplished, for example, using pumps, hydrostatic pressure, capillary forces, and the like.

In various embodiments, the fluid charging systems disclosed herein may be used to provide charged fluid to microfluidic processing networks and systems. A charged fluid may be mixed with other fluids in a microfluidic processing network or system. Microfluidic processing networks and systems in which fluids may be mixed are described, for example, in United States Patent Application Publication Nos. 2005/0092681, 2005/0272144, 2008/0277494, 2010/0015606, 2010/0029512, 2010/0109320, and 2010/0297748, which are all incorporated by reference herein. The fluid charging systems disclosed herein may be in fluid communication with microfluidic processing networks and systems such as those described in these documents.

In various embodiments, the fluid charging systems disclosed herein may be used to provide charged fluid to microfluidic processing networks and systems comprising liquid bridges. United States Patent Application Publication Nos. 2008/0277494, 2010/0015606, 2010/0029512, 2010/0109320, and 2010/0297748, which are all incorporated by reference herein, describe microfluidic processing networks and systems comprising liquid bridges. A liquid bridge is a device in which liquid droplets are formed. The droplets formed in a liquid bridge are enveloped in an immiscible carrier fluid. Generally, a liquid bridge is formed by an inlet in communication with a chamber that is filled with immiscible carrier fluid. The carrier fluid is immiscible with fluid droplets flowing through the inlet into the chamber. The fluid droplets expand until they are large enough to span a spatial gap between the inlet and an outlet in communication with the chamber. Droplet formation is accomplished, for example, by adjusting flow rate or by joining one or more additional fluid droplets to a first fluid droplet, resulting in formation of an unstable liquid bridge between the inlet and the outlet that subsequently ruptures from the inlet. After rupturing from the inlet, the fluid droplet enters the outlet, surrounded by the carrier fluid from the chamber.

The fluid charging systems disclosed herein may be configured to provide charged fluid to a liquid bridge. For example, a fluid sampling device of a fluid charging system may be in fluid communication with a liquid bridge. In various embodiments, a liquid bridge may be configured to segment a charged fluid into droplets. In various embodiments, a liquid bridge may be configured to mix droplets of charged fluid with droplet of other fluid (that may be uncharged or charged, for example, as described herein) that is miscible with the charged fluid. As used herein, the term "droplet" refers to a relatively small microfluidic quantity or plug of liquid as it is suspended and/or flows in an immiscible carrier liquid in a conduit or chamber, such as, for example, in a microfluidic processing network or system.

Further provided herein is a method of mixing droplets using electrostatic charging of droplets. In some embodiments a charged droplet, for example a statically charged droplet, may be directed toward a second droplet. The droplet may be charged using the method and system provided herein. The second droplet may be charged or uncharged. As the charged droplet approaches the second droplet, the charged droplet may induce charge separation in the awaiting second droplet. The charge separation may then cause the charged droplet and the second droplet to become more attracted to each other and may facilitate the combining of the two droplets. The charge separation in the second droplet, together with the charged droplet may cause the two droplets to mix in a more efficient manner than when both droplets are uncharged. In some embodiments, a charged droplet may be combined with at least two droplets, in which at least one droplet may be charged. In some embodiments, a first droplet may be charge and the second and third droplets may be uncharged. In some embodiments, a first droplet and a second droplet may be charged and the third droplet may be uncharged.

In some embodiments, the droplets may be charged or uncharged to prevent droplets from combining. In some embodiments, charging droplets may be useful in sorting droplets by preventing droplets from combining or by dictating which path the droplet may flow through.

Other embodiments, of fluid charging systems are described in US. Ser. No. 61/473,317, which is incorporated herein by reference in its entirety.

Fluid Pumping System

Figure 6:
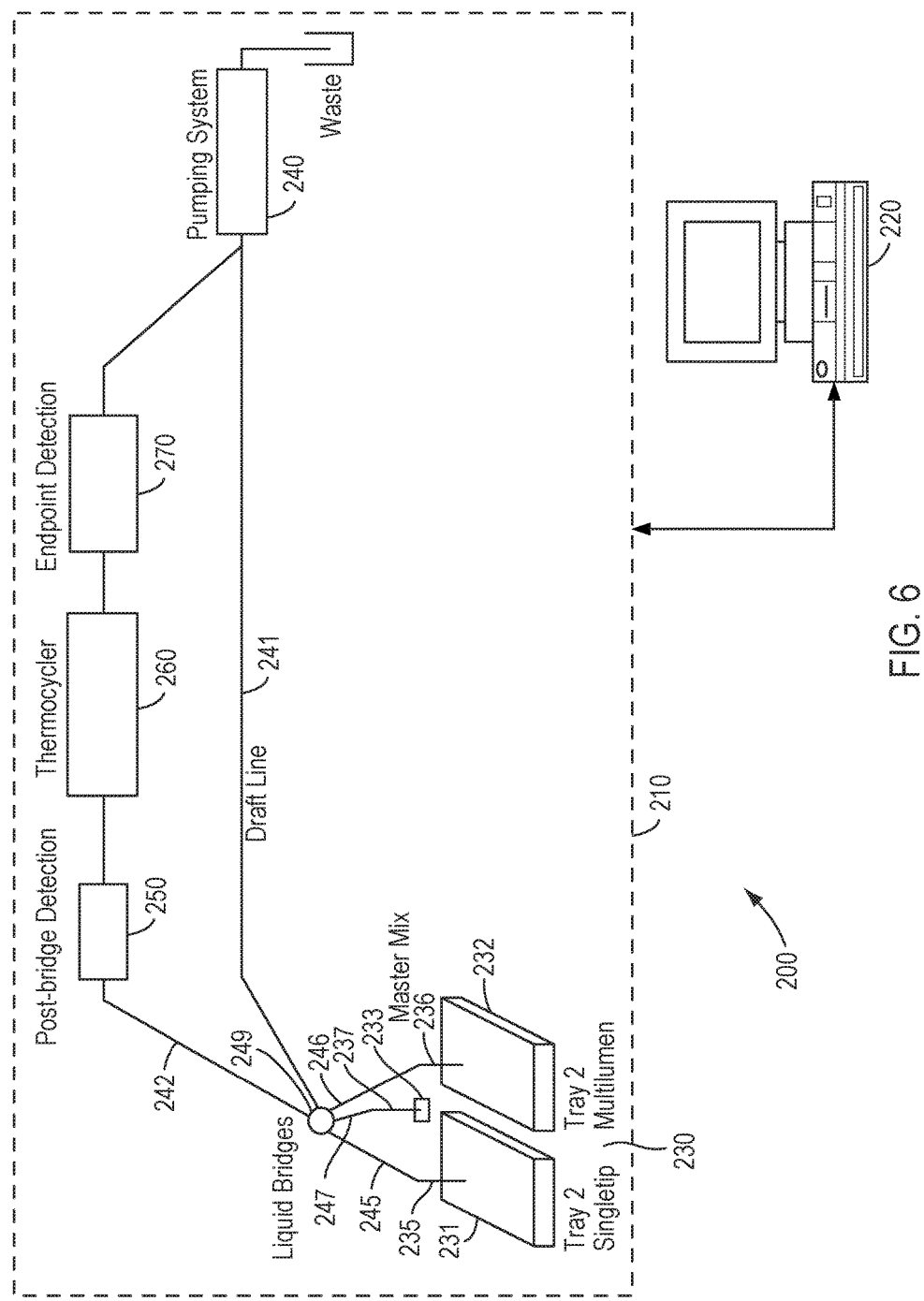
FIG. 6 is a schematic diagram showing a system for high throughput PCR amplification and analysis.

FIG. 6 is a schematic diagram showing a system 200 for high throughput PCR amplification and analysis, in accordance with various embodiments. System 200 includes PCR system 210 and processor 220. PCR system 210, in turn, includes liquid handling system 230, fluid pumping system 240, post-bridge detection system 250, thermocycler 260, and endpoint detection system 270. The system 200 operates under the principal of continuous flow. A constant flow of oil is maintained through the thermocycler (TC line 242) and this flow of oil carries mixed droplets. It is required that the flow upstream of the liquid-bridges (from sample-tips to bridges) be faster than the flow through the thermocycler in order to meet throughput demands A draft line 241 is fitted to the bridge and bleeds off excess oil. The TC line 242 and the draft line 241 both operate at fixed flow rates. It is required that these lines be controlled as the addition of droplets to the lines increases the pressure drop along each line. The combined flow in the TC line 242 and draft line 241 equals that of the master-mix, sample and primer-probe lines.

In addition the pumping system incorporates a number of subsystems for priming the system with oil and bleeding it of air. FIG. 6 shows a general schematic (for a single line system) showing the TC Line 242, the Draft Line 241 and where the hardware components are located.

If a PCR system operates under continuous flow, moving the system through air to move from well-to-well would cause air to be drawn into the system. This is avoided through the use of sheathing/flap valves. These larger bore tubes are fitted around the sampling tubes and wrap them in oil. The continuous flow of oil into the sheathing (driven by 3 independent sheathing pumps) matches (or slightly exceeds) the flow being drawn into the system tips insuring that the continuous flow lines are always wrapped in oil. Hence the tips can move freely from well to well without drawing any air into the system.

Liquid Bridge Technology

In various embodiments, a liquid bridge configured to segment charged fluid withdrawn from a fluid vessel into droplets comprises a first inlet port in fluid communication with a fluid sampling device, a second inlet port in fluid communication with a source of immiscible fluid, an outlet port, and a chamber. The inlet ports and the outlet port open into the chamber and may be structured and positioned so that fluid instability in fluid droplets formed between the first inlet port and the outlet port segments the fluid withdrawn from the fluid vessel into fluid droplets separated by the immiscible fluid. The fluid droplets may be withdrawn from the chamber through the outlet port.

Figure 7A:
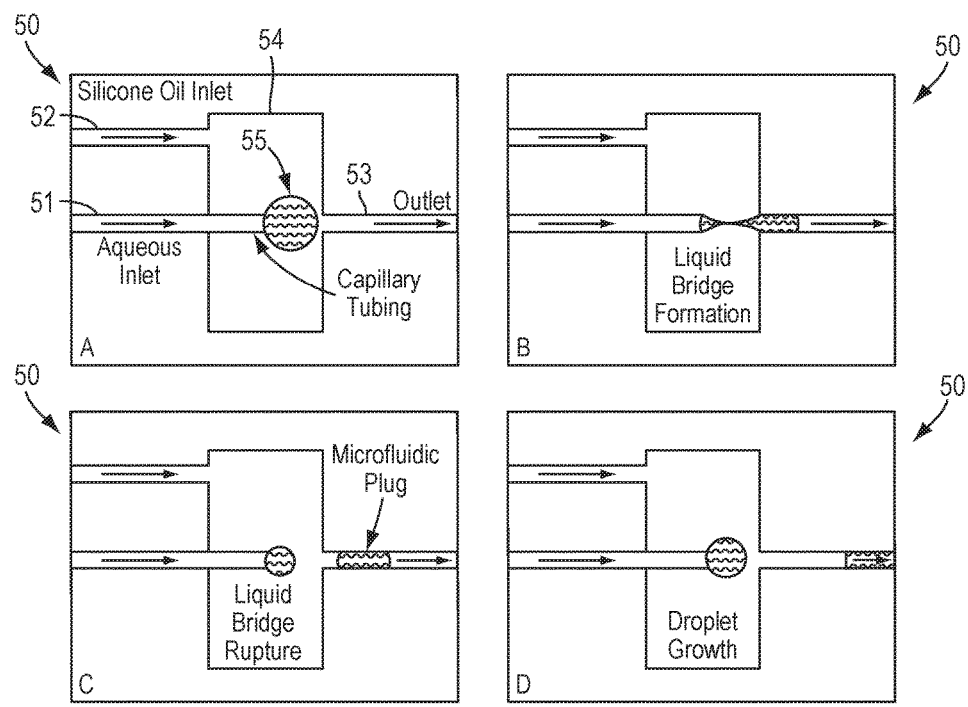
FIGS. 7A & 7B illustrate various embodiments of a liquid bridge.
Figure 7B:
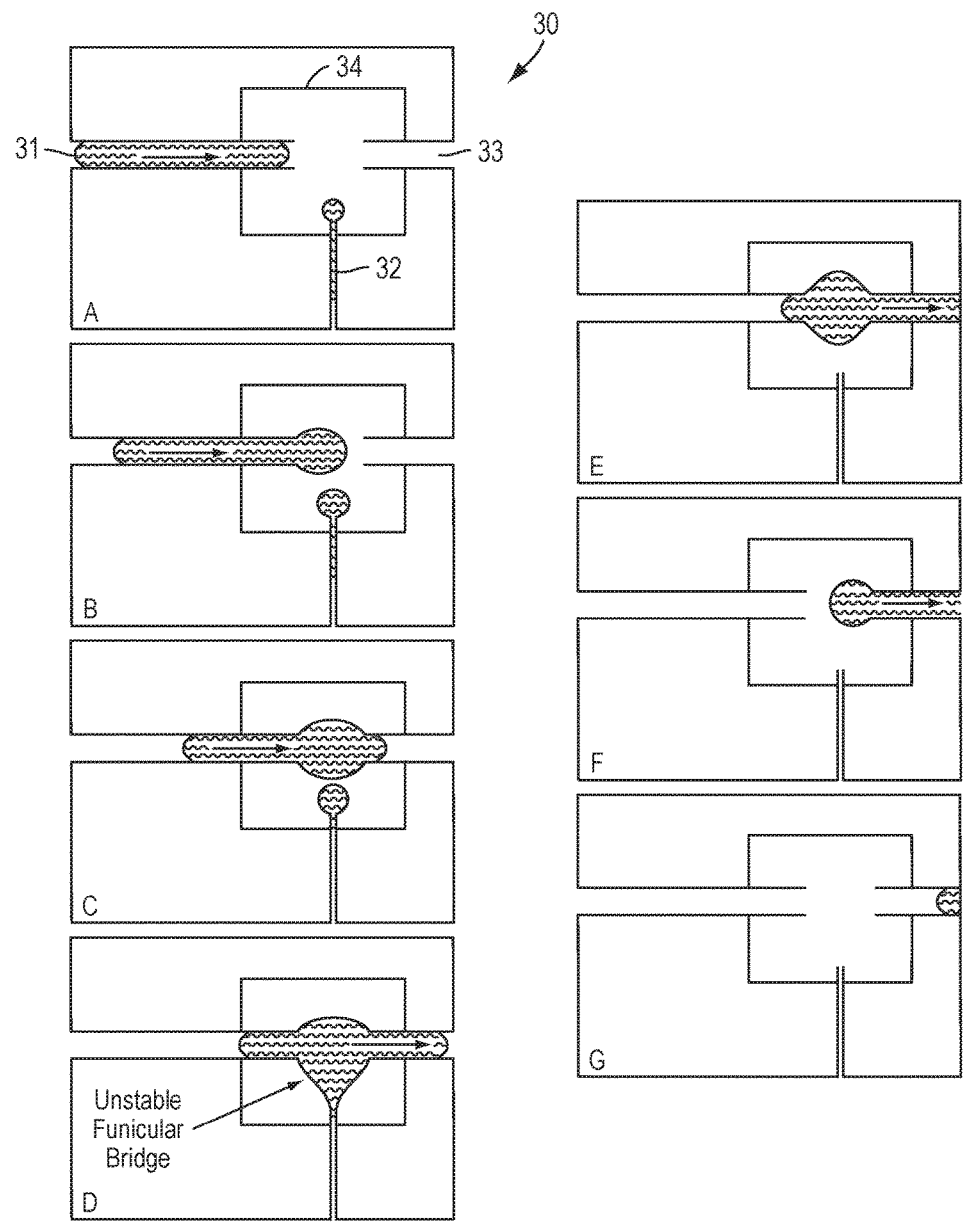

In various embodiments, a liquid bridge configured to mix charged fluid withdrawn from a fluid vessel in a fluid charging system with one or more additional fluids that may be miscible with the charged fluid comprises a first inlet port in fluid communication with the fluid sampling device, one or more additional inlet ports in fluid communication with sources of the one or more additional fluids, an outlet port, and a chamber. The inlet ports and the outlet port open into the chamber and may be structured and positioned so that first fluid droplets formed at the first inlet port contact and mix with one or more additional fluid droplets formed at the one or more additional inlet ports, thereby forming unstable funicular bridges of mixed fluid. The unstable funicular bridges rupture, thereby forming mixed fluid droplets separated by immiscible carrier fluid that are withdrawn from the chamber through the outlet port. The net charge carried by the fluid withdrawn from the fluid vessel improves the mixing of the charged fluid with the one or more additional fluids. One embodiment of a liquid bridge is shown in FIGS. 7A & 7B (from Stokes LB Patent application). A more detailed description of a liquid bridge may be found in United States Patent Applications Nos. 2008/0277494 and 2010/0029512 and PCT Application Nos. PCT/IE07/000013 and PCT/US10/24180, each of which is incorporated by reference in their entirety.

In various embodiments, a liquid bridge configured to mix charged fluid withdrawn from a fluid vessel in a fluid charging system with one or more additional fluids that are miscible with the charged fluid comprises a chamber, one or more inlet ports, a first outlet port, and a second outlet port. The inlet ports and the outlet ports may open into the chamber. An inlet port may be in fluid communication with a fluid sampling device and sources of one or more additional fluids. The inlet ports may serially provide fluid droplets of the charged fluid withdrawn from the fluid vessel and the one or more additional fluids, wherein the droplets may be separated by an immiscible carrier fluid. The first outlet port may be configured to withdraw a portion of the immiscible carrier fluid entering the chamber. The inlet ports and the outlet ports may be structured and positioned so that trailing droplet transporting through the inlet port contact and mix with leading droplets formed at the inlet port in the chamber, thereby forming mixed fluid droplets that may be withdrawn from the chamber through the second outlet port separated by immiscible carrier fluid. The net charge carried by the fluid withdrawn from the fluid vessel improves the mixing of the charged fluid with the one or more additional fluids.

In some embodiments the liquid bridge comprises at least two channels, tubes, capillaries, or any other suitable conduit for providing fluid communication between a reservoir containing a fluid and a liquid bridge. In some embodiments, the mechanism may be PTFE tubes. The PTFE tubes may be layered so that multiple tubes are stacked one on top of the other. In some embodiments, the conduits may be stacked using a support. In some embodiments, the support or washboard may smooth. Alternatively, the washboard may be on a support/washboard that has undulations. The undulating pattern may create undulations in the conduits themselves, wherein these undulations may then provide natural stops for the droplets flowing in the tubes or conduits, for example sample and assay droplets. In such a manner, the droplets may be stopped or held in position prior to entry into the liquid bridge. The holding of holding/stopping of the droplets may allow for all necessary droplets to come into the liquid bridge prior to being mixed together. In some embodiments, 10 individual PTFE parts may be used. In some embodiments, one PTFE coated aluminum part may be used. An example of a washboard/support may be found seen in FIG. 8. In some embodiments, the liquid bridge my further include a PTFE tube having an internal diameter that widens to slow the droplet speed as it approaches the liquid bridge.

Figure 9A:
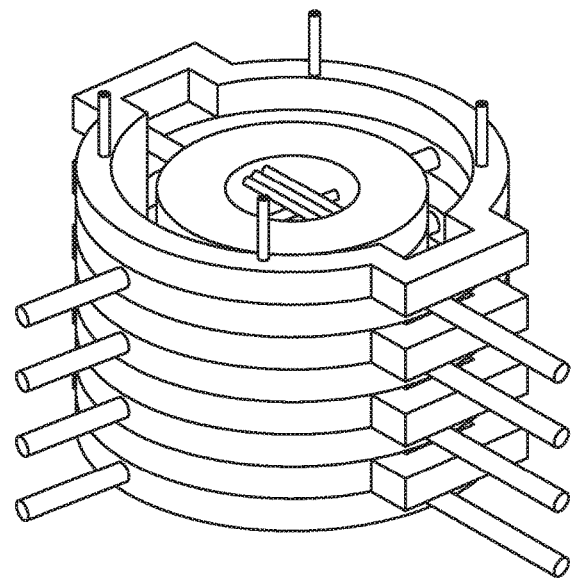
FIGS. 9A and 9B show examples of stacked liquid bridges.
Figure 9B:
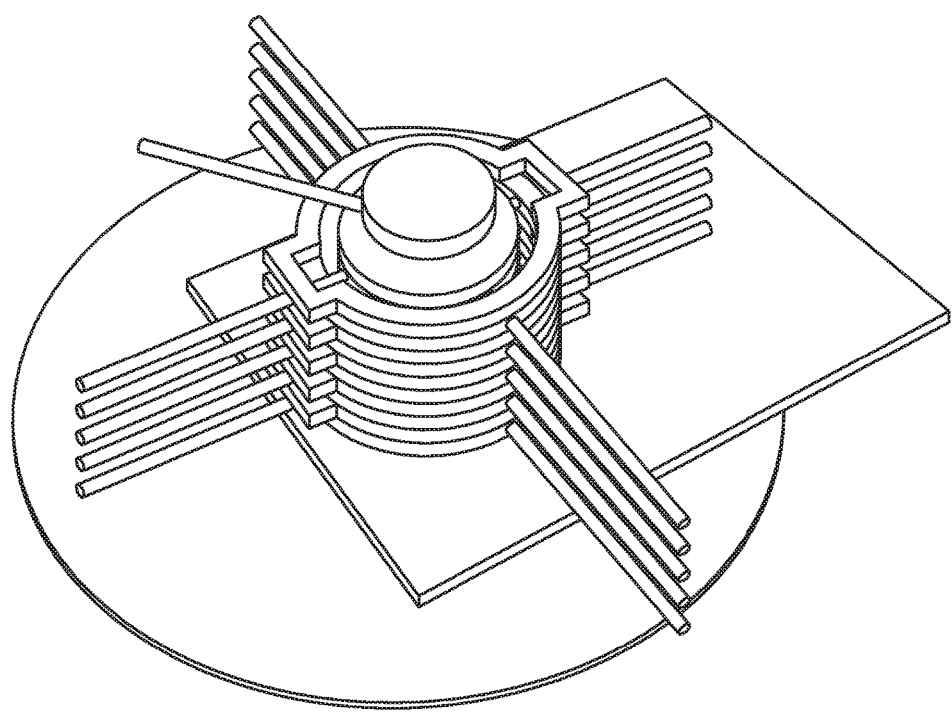

In some embodiments, the liquid bridge may be a single bridge. In some embodiments, the bridges may be stacked by placing individual bridges on one another. FIGS. 9A & 9B show examples of an isolated stacked liquid bridge and a stacked liquid bridge as connected to the system, respectively. In some embodiments, any number of bridges may be combined to form a stacked liquid bridge having a single bridge cavity. In some embodiments, a single cavity may be constructed from any suitable number of bridges. In some embodiments, a single cavity may include at least 2, at least 4, at least 8, at least 12, at least 16, at least 20, at least 24, at least 30, at least 50, at least 75, at least 90, at least 96, at least 120 bridges.

Figure 10A:
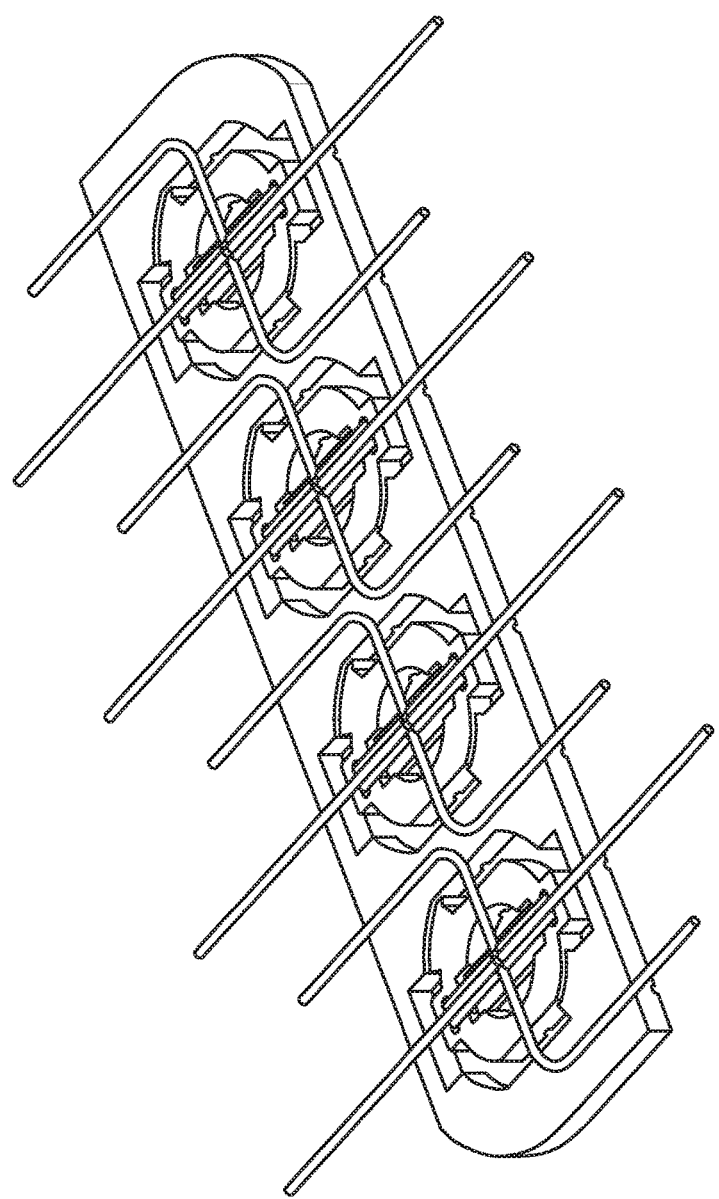
FIGS. 10A and 10B show examples of liquid bridge substrates.
Figure 10B:
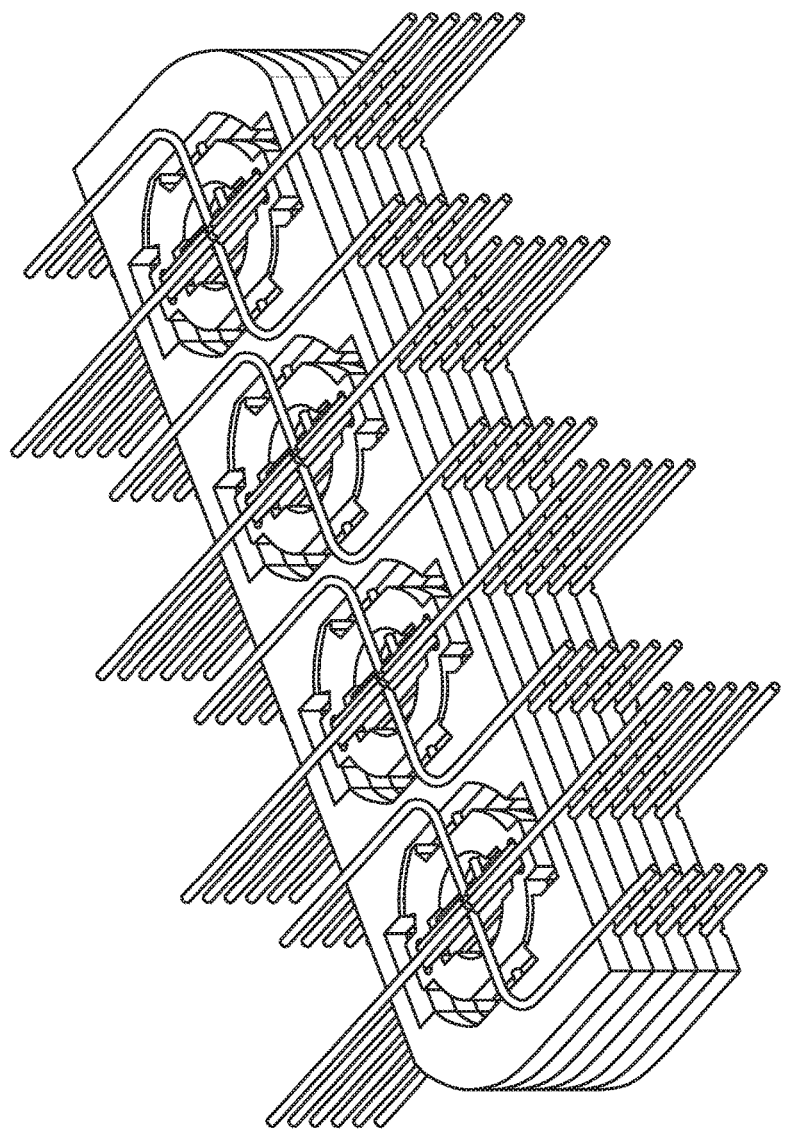

In some embodiments a combined liquid bridge cavity may be formed by machining a substrate containing at least one "bridge". Such a substrate may be a precision machined substrate, such as a polycarbonate piece onto which features are assembled. The substrate may be machined such that features are on both sides of the substrate to aid in stacking of substrates. FIG. 10A shows a single substrate with four bridges. FIG. 10B shows multiple substrates stacked upon each other.

The capillaries, tubes, channels or other suitable mechanism for providing for fluid communication between a reservoir and the bridge may be generated by thermoforming the PTFE capillaries. The substrate may be designed to have curved channel paths into which tubing is bonded. Thermoforming involves placing tubes into geometric paths similar to the paths found in the substrate, applying a stop band at a precise location, heating to 240 degrees Celsius for 30 minutes and then cooling the tubes. When removed, the tube retains the shape of the path. The preformed tubing can then be assembled into the substrate quickly. The stop bands formed on the tubes prevents the tubing tips from protruding too far into the liquid bridge.

Figure 11:
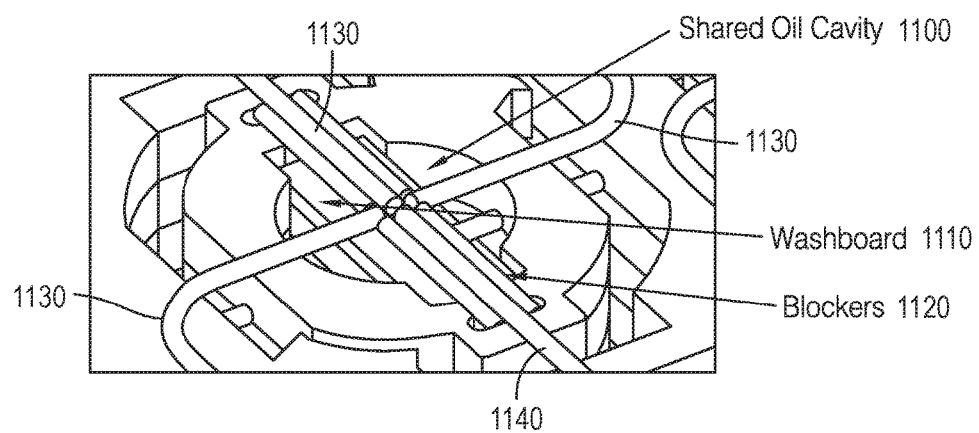
FIG. 11 shows one example of a shared oil cavity.

The stacked liquid bridge may have a geometry that includes a shared oil cavity as seen in FIG. 11. As seen in FIG. 11, each "bridge" of the stacked bridge comprises a washboard 1110, inlet tubes 1130 and outlet tube 1140. The bridges include a shared oil cavity 1100 in which oil is free to flow between the bridges. Additionally, blockers 1120 may be present to prevent movement of droplets between bridges. However, oil is free to flow in the shared oil cavity. Therefore, the blockers may be spaced such that they may restrict movement or loss of droplets during mixing. Additionally, in some embodiments, the blockers may serve to close off the mixing zone. The spacing between the blockers and the liquid bridge is small enough to prevent droplet loss from the liquid bridge into the shared oil cavity but to allow oil to flow into the liquid bridge.

The droplet stream leaving the liquid bridge or bridges (in the case of a stacked liquid bridge) may be divided into packets. The droplet stream may be divided based upon the time-stamp at which the robotics takes a sample. For convenience these packets are called carriages. The use of carriages—where the spacing between carriages is at least twice that between droplets—permits easier identification of individual droplets and indeed easy identification of errors in the droplet stream. For example droplet 2 of carriage 2 (with 5 droplets per carriage) may be identified more easily than droplet 12 of a continuous stream. Similarly errors can be easily identified. If only 4 droplets are present in a carriage of 5 then it is clear an error has occurred (droplet merging); if 6 are present then a droplet has not mixed or has mixed and then split into two.

Further description of the structure and operation of segmenting liquid bridges and mixing liquid bridges is presented in United States Patent Application Publication Nos. 2008/0277494 and 2010/0029512, which are incorporated by reference herein.

Post-Bridge Error Correction

Figure 12:
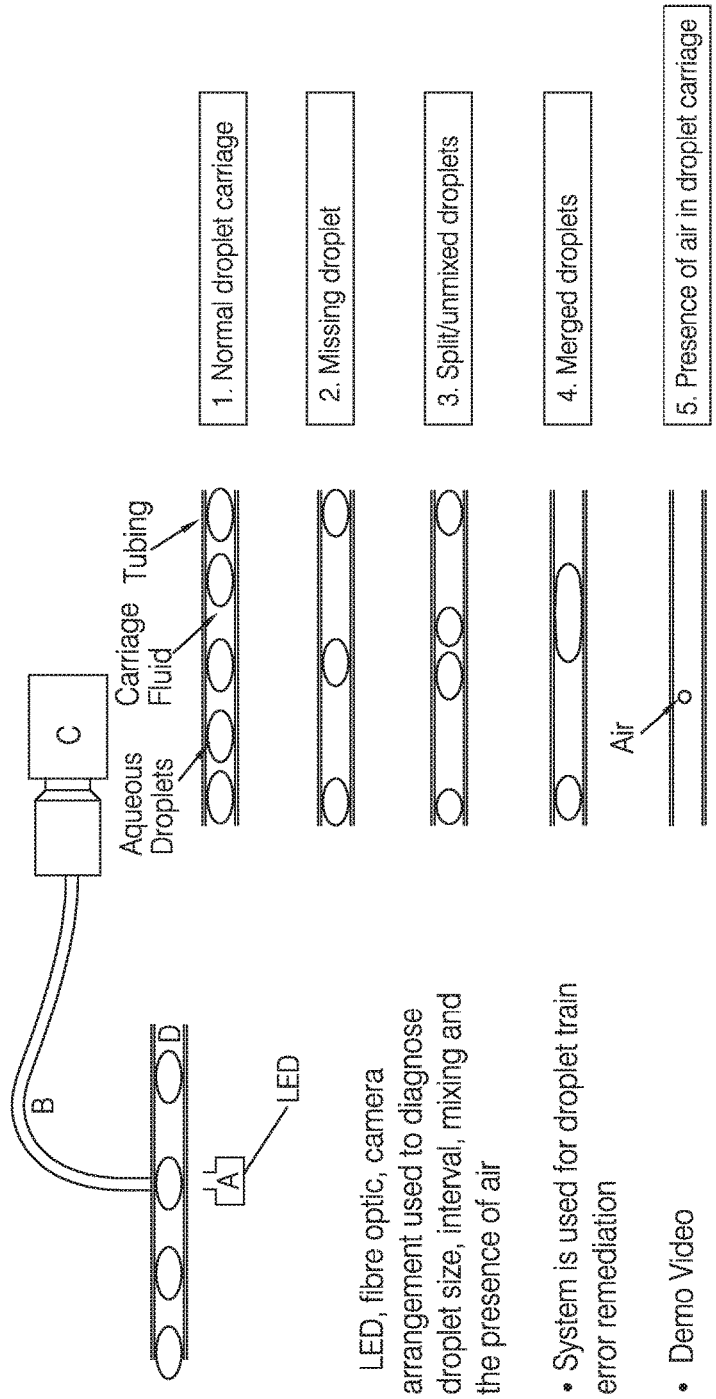
FIG. 12 shows one embodiment of a post bridge diagnostic system.

In some embodiments of the system provided herein, the system further comprises a post-bridge diagnostic system. In some embodiments, the system may be used to detect normal droplets, missing droplets, unmixed droplets, merged droplets. In some embodiments the system may be used to detect the presence of air in a droplet carriage. FIG. 12 is an example of a post bridge droplet diagnostic system.

In some embodiments, the post-bridge detection system is a post-bridge error correction detection system. In some embodiments, the post-bridge correction system may include at least one light emitting diode (LED). In some embodiments, the system may include an array of blue light emitting diodes (LEDs) illuminating the output line from the bridges (between the liquid bridges and the thermocycler). Any suitable excitation source may be used including but not limited to, LEDs, laser, or any other suitable excitation source. In some embodiments, at least one, at least two, at least three detectors may be used to monitor light emitted from a droplet. In some embodiments, the detectors may be PMTs, or cameras, or detector arrays. In some embodiments, three cameras (for example Basler cameras) may used to monitor the fluorescent wavelengths excited by the blue LEDs. In some embodiments, at least one, at least two, at least three wavelengths may be monitored. In some embodiments, the components, dyes, fluorescence emission detected may be from the same is each droplet exiting the detection system. In some embodiments, two of the emissions detected from the droplet may be of the same wavelength and a third may be of a different wavelength. For example purposes only, the system may be able to detect FAM/VIC in the primer-probes droplet, ROX in the Master-Mix droplet and a third dye (i.e. ALEXA) added to the sample droplet as a reference. If the detection system picks up all three wavelengths from a droplet, then this is considered a mixed and valid droplet. However in some cases the bridges will not mix a droplet correctly. This is found by determining that one or more of the components are missing from the main droplet. In the event an error occurs with a single droplet (or carriage) then this droplet (or the entire carriage) will be re-sampled. Additionally, the detection system may be used to measure a level of fluorescence in a droplet to aid in sorting of droplets based on the droplet contents.

In some embodiments of the system, the post-bridge detection system may include at least one LED or an array of LEDs illuminating the output line from the at least one liquid bridge or at least one stacked liquid bridge but before the thermocycler. In some embodiments, the detection system uses any suitable excitation source, including but not limited to lasers, including both fiber-coupled and freespace, electromagnetic radiation, white light, filtered light Opposite the LEDs are fibers running to an array. One cameras (Basler) monitors the fiber-array and detects droplets passing the LEDs through variations in light intensity. The system may then count the number of droplets in a carriage and compare this to the number expected. If the numbers do not match an error will be indicated and the carriage will be re-sampled.

In some embodiments, the droplet stream leaving the bridges may be divided into packets or carriages (based upon the time-stamp at which the robotics takes a sample. A carriage is defined when the spacing between carriages or droplet trains is at least twice the spacing between droplets. By dividing the droplets into carriages, identification of individual droplets and identification of errors in the droplet stream may be facilitated. For example purposes, Droplet 2 of Carriage 2 (with 5 droplets per carriage) may be identified more easily than Droplet 7 of a continuous stream. Similarly errors can be easily identified. If only 4 droplets are present in a carriage of 5 then it is clear an error has occurred (droplet merging); if 6 are present then a droplet has not mixed or has mixed and then split into two.

In some embodiments, the number of droplets in a carriage/droplet stream is known and/or expected. In some embodiments, the number of droplets in a carriage is unknown. In some embodiment, any change in the number of droplets in a carriage indicates an error, including more droplets than expected, less droplets than expected or a droplet from one carriage being present in a second carriage. The presence, absence or dual droplet errors may then be resolved by indicating that an error has occurred. This indication may be that the whole droplet stream/carriage is erroneous, the carriage and the adjacent carriage are erroneous, one droplet in the carriage is erroneous, or multiple droplets in the carriage are erroneous.

In some embodiments, the system may droplet detection may be done using fluorescent detection. In some embodiments instead of detecting the fluorescence emissions the absorbance of the droplet can be detected. In such an embodiment, a single camera, LEDs and related fibers may be used to first count all droplets in a carriage. In some embodiments, the detection system may then be used to also acquire the peak width which corresponds to the length of a droplet. In some embodiments, the system may acquire the diameter of the droplet, the volume of the droplet, size of the droplet or any other suitable parameter. In such an embodiment, if a carriage has more or less droplets than a predetermined amount of droplets/carriage then the carriage fails and is rejected and re-sampled. In some embodiments, the length of the droplet will vary depending on how many of component droplets are present and then combined by a mixer or liquid bridge into a mixed droplet. In some embodiments, the carriage may be analyzed and the standard deviation calculated. The standard deviation may then be divided by the mean of the droplets in a carriage. In some embodiments, the carriage may passed or fail if the result of the calculation is either below or above a set threshold. The carriage is re-sampled if it is failed. In some embodiments, error detection may occur using a single droplet as opposed to a droplet carriage.

In some embodiments, the passage of a droplet between the light source and the detection system may be used as a detection method. The passage of a droplet between the light source and the detection system may cause a unique signature away from baseline measure. Although this signature may vary, in some embodiments, the observed signal may be a sharp spike (sometimes followed by a signal slightly above baseline) and then a sharp trough. The leading edge of the droplet is focusing light intensity onto the detector, resulting in the spike. The slightly higher signal may be a result of the difference in refractive index between the oil and aqueous signal. The trailing edge of the droplet may focus light intensity away from the detector resulting in a sharp trough. As the droplet clears the detector the baseline returns to normal. In some embodiments, the leading edge of the droplet may lead to light being directed away from the detector and the trailing edge focusing light on the detector. In some embodiments, the signal may be a peak, a trough, both a peak and trough, or an increase in signal from baseline wherein the signal plateaus for a period of time followed by a return in signal to baseline or a decrease from baseline, a period of plateau, following by an increase back to baseline. In some embodiments, air droplets or any other type of droplet may be identified using the methods and system described herein based on the unique signature of the air droplets.

In some embodiments, the light source is white light or filtered light and a non-filtered detection source is used. The wavelength of the light used may or may not affect the shape of the droplet signatures detected. In some embodiments, the system may be used to determine if all the components have combined into a mixed droplet based on the spacing between the spikes which may correlate to the width of the droplets.

In some embodiments, fluorescence or absorbance detection may be used in conjunction with and applied to endpoint measurements. This may act as an additional quality control measure to pick up any errors that are not caught by the post-bridge error detection. In such a manner, the combination of factors may be used to highlight any suspect data.

In some embodiments, the endpoint detection system may include a free-space spectrograph system. In some embodiments, the acquisition hardware is a Hamamatsu Orca camera. The 96 thermocycler lines are illuminated by a 488 nm laser-line. This laser-line is imaged by the spectrograph/camera and resolved into its constituent wavelengths. Appropriate wavelengths may then be measured according to the contents of the droplets. Droplets may be identified based upon the time-stamp generated by the post-bridge detection module and raw fluorescent data is then generated for droplet. In some embodiments, spectral compensation may then be applied to compensate for dye bleed through. In some embodiments, other methods of compensation may be used to compensate for dye bleed through, including background/baseline subtraction, or any other suitable method of compensation.

In order to maintain the high throughput of a continuous flow PCR system, the PCR system needs to be able to detect fluorescence in two or more micro-channels at the same time. Measuring fluorescence across two or more micro-channels imposes a number of limitations on an endpoint detection system.

For example, as the number of number of micro-channels is increased, the field of view of the detector also needs to increase. These micro-channels can be closely bundled or aligned together in an array of transparent micro-channels or tubes. However, a wall of some thickness has to be maintained between tubes to prevent crosstalk between adjacent micro-channels. As a result, the field of view of the detector is a function of the tube diameter and tube array wall thickness. In order to maintain a high fluorescence collection efficiency from the tubes on the edges of the tube array, an increased beam length can be used. Increasing the beam length from the tube array to the detector may increase the overall physical size of the endpoint detection system.

In some embodiments, the system may be able to detect spectral information from two or more micro-channels in a single time step. However, in order to assign that spectral information to the correct sample, the particular tube emitting that spectral information may be located in the tube array. As result, the detection system may provide spatial information in addition to spectral information.

Figure 13:
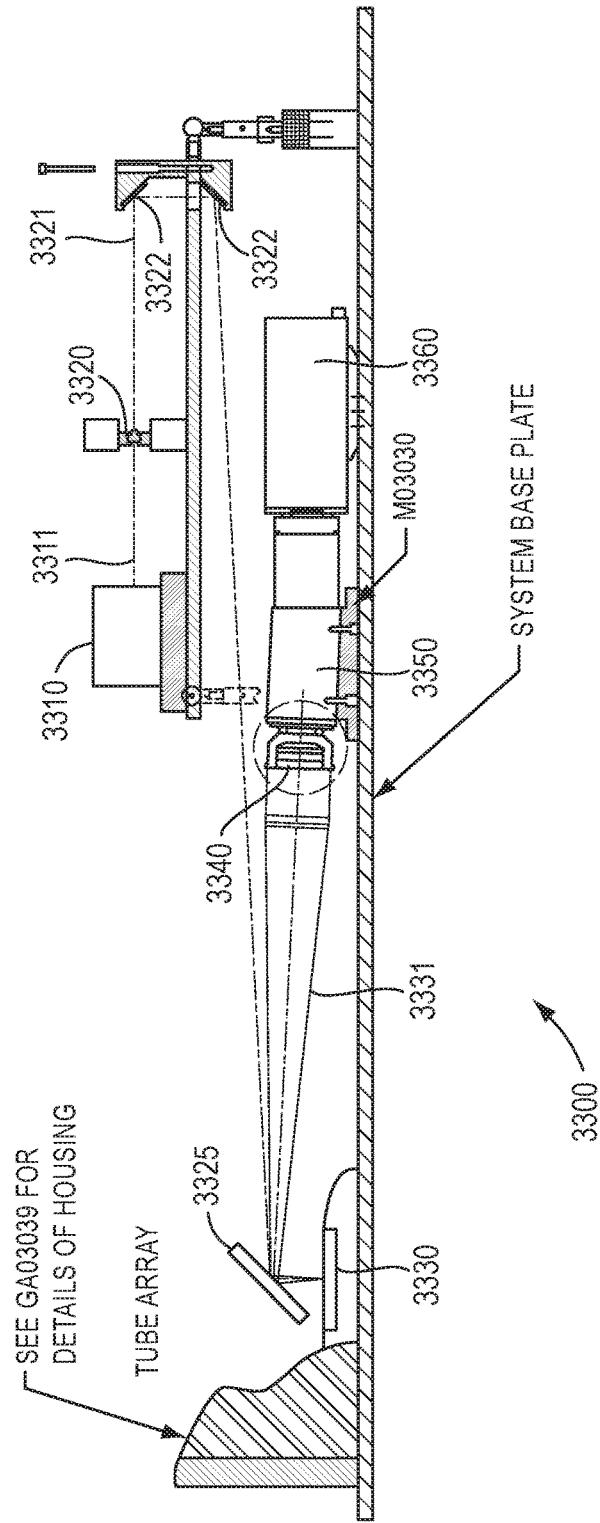
FIG. 13 is one embodiment of a schematic diagram of a side view of a system for detecting spectral and spatial information in a continuous flow PCR system.

FIG. 13 is a schematic diagram of a side view of a system 3300 for detecting spectral and spatial information in a continuous flow PCR system, in accordance with various embodiments. System 3300 includes laser 3310, line generator 3320, tube array 3330, imaging lens 3340, spectrograph 3350, and imager 3360. Laser 3310 emits incident beam of electromagnetic radiation 3311.

Line generator 3320 receives incident beam 3311 from laser 3310. Line generator 3320 transforms incident beam 3311 into incident line of electromagnetic radiation 3321. In other words, line generator 3320 converts the power distribution of incident beam 3311 from a non-uniform distribution to a uniform distribution. Line generator 3320 is a Powell lens, for example. In various embodiments, line generator 3320 is a diffractive line generator.

Tube array 3330 receives incident line 3321 from line generator 3320. Tube array 3330 includes one or more transparent tubes in fluid communication with one or more micro-channels of a PCR system. In various embodiments, one or more optical elements 3322 are placed between line generator 3320 and tube array 3320 to steer incident line 3321 from line generator 3320 to tube array 3330. As shown in FIG. 13, one or more optical elements 3322 allow system 3300 to be package in an overall smaller volume, for example. In various embodiments, mirror 3325 is also placed between line generator 3320 and tube array 3330 to steer incident line 3321 from line generator 3320 to tube array 3330. Mirror 3325 allows tube array 3330 to be positioned horizontally in system 3300, for example.

Imaging lens 3340 receives reflected electromagnetic radiation 3331 from tube array 3330 and focuses reflected electromagnetic radiation 3331. In various embodiments, one or more optical elements (not shown) are placed between tube array 3330 and imaging lens 3340 to steer reflected electromagnetic radiation 3331 from tube array 3330 to imaging lens 3340. In various embodiments, mirror 3325 is placed between tube array 3330 and imaging lens 3340 to steer reflected electromagnetic radiation 3331 from tube array 3330 to imaging lens 3340. Imaging lens 3340 is a wide-iris lens with a variable aperture, for example. In various embodiments, imaging lens 3340 includes one or more optical filters (not shown). The one or more optical filters remove reflection of incident line 3321 from reflected electromagnetic radiation 3331, for example.

Spectrograph 3350 receives the focused reflected electromagnetic radiation (not shown) from the imaging lens 3340. Spectrograph 3350 detects a spectral intensity from the focused reflected electromagnetic radiation. In some embodiments, spectrograph 3350 can detect spectral wavelengths between 400 and 800 nanometers, for example. In some embodiments, the spectrograph may be such that it can detect any suitable wavelength.

Imager 3360 receives the focused reflected electromagnetic radiation from imaging lens 3340. Imager 3360 detects a location of the spectral intensity. Imager 3360 is a CCD camera, for example.

In various embodiments, system 3300 also includes a processor (not shown). The processor receives the spectral intensity from spectrograph 3350 and receives the location from imager 3360. The processor determines an intensity value for a sample moving through tube array 3330 from the spectral intensity and the location.

Thermocycling

In some embodiments, the system may be in fluid communication with a thermocycler. In some embodiments, the system operates under the principal of continuous flow. In some embodiments, a constant flow of oil may be maintained through the thermocycler (TC Line) and this flow of oil may carry mixed droplets. In some embodiments, the flow upstream of the liquid-bridges (from sample-tips to bridges) is faster than the flow through the thermocycler in order to meet throughput demands A Draft Line may be fitted to the bridge which bleeds off excess oil. The TC Line and the Draft Line both operate at fixed flow rates. It is required that they be controlled as the addition of droplets to the lines increases the pressure drop along each line. The combined flow in the TC Line and Draft Line equals that of the master-mix, sample and primer-probe lines. In addition the pumping system will incorporate a number of subsystems for priming the system with oil and bleeding it of air. FIG. 6 shows a general schematic (for a single line system) of showing the TC Line, the Draft Line and where the hardware components are located. Also shown in FIG. 7 is a schematic of our proposed software architecture.

The thermocycler consists of 4 24-line thermocyclers. Each block is preceded by a pre-heat block. Each block will be maintained at its set-point using PID control.

Electrowetting/Vaporization

In some embodiments of the system, thermocycler may be used thermal blocks may be used with or without other materials to manipulate the thermal gradient of samples as they enter/exit thermal zones. In some embodiments, the use of an in-line water bath to provide a thermal step and more effective electrical discharge of tubing prior to entering the preheat stage of the thermal cycler. In some embodiments, a water bath may be used to replace the existing preheat block.

In some embodiments, any static charge on the tubing entering the preheat section of the thermocycler may be controlled through the use of static generators and/or electrical circuits. In some embodiments, electrically conductive PTFE tubing may be used to provide more effective electrical discharge of the tubing. In some embodiments, non-anodized components in thermocycler assemblies may be used to provide more effective electrical discharge of the tubing. In some embodiments, additives may be added to the oil to increase electrical conductivity, or the use of an alternative oil with better electrical conductivity. In addition, in some embodiments, surfactants may be used to manipulate the droplet-oil interfacial tension which would provide a more resistant interface to vaporization. In some embodiments of the system, the system may allow for pumping/processing of samples through the thermocycler under positive pressure. In some embodiments, environmental control of humidity/local external pressure on the system may be controlled to produce less favourable conditions for vaporization.

Detection

In some embodiments of the system, endpoint detection may occur. In some embodiments, the system may include real-time detection. In some embodiments, the system may include a free-space Spectrograph system. For example, the acquisition hardware may be a Hamamatsu Orca camera. The 96 thermocycler lines may illuminated by a 488 nm laser-line. This laser-line may be imaged by the spectrograph/camera and resolved into its constituent wavelengths. In some embodiments, appropriate wavelengths may be measured according to the contents of the droplets. Droplets may be identified based upon the time-stamp generated by the post-bridge detection module and raw fluorescent data may then be generated for droplet. Spectral compensation may then be applied to compensate for dye bleed through.

In another embodiment a single detector could be used, i.e a single camera and filter wheel or a spectral camera based system similar to our end-point system with the addition of optical fibers. In some embodiments, the detector may be a spectrograph, filterwheel/camera combo, acousto-optical tuneable filter and camera, photo-diode, photo-diode array, PMT, as well as CCD/CMOS/digital cameras.

Droplet Dispensing or Collection

Using a microfluidic valve and a liquid bridge, the flow of droplets can be controlled. For example purposes only, a droplet of interest could be identified where the droplet is located in a train of droplets. In such an embodiment, the droplet of interest could be identified based on an optical detection system, wherein the optical detection system may identify the droplet of interest based on any suitable parameter, including but not limited to dye color and/or concentration, turbidity, optical density, viscosity, charge, polarity, light diffraction of diffusion, or any other suitable parameter. Once the droplet of interest has been identified by the detection system, a signal may be sent to a microfluidic valve located upstream from the detection system to direct the flow of the droplet through the system. In some embodiment, the valve may be in fluid communication with at least two microfluidic channels, wherein a single droplet is permitted to travel through the channel at any given time. In some embodiments the valve may be in fluid communication with at least three microfluidic channels. In some embodiments, one of the microfluidic channels may be in fluid communication with a collection system for collecting the droplets. The droplet switching system may works as follows. In some embodiments, a droplet generated by the liquid bridge is sent through a primary microfluidic channel where a parameter of interest may be detected. The droplet may be an aqueous droplet surrounded by an immiscible fluid, such as oil. Alternatively, the droplet may be an emulsion droplet of an oil droplet surrounded by an immiscible fluid, wherein the immiscible fluid is an aqueous fluid. The characteristics of the droplet determine if the system dictates that the droplet is sent down secondary channel A to be collected or through secondary channel B for either further processing or for collection as waste. Once the droplet passes through the valve into its proper secondary channel, a new droplet passes through the detection system. Again, the system may detect the presence or absence of a parameter of interest and direct the second droplet to its proper secondary channel. In some embodiments, there is a 30 second delay between the droplets for the droplet detection system.

Optics

The optics of the system is such that the system can simultaneously measure from 96 channels. A suitable embodiment of the optical system may be found in U.S. patent application Ser. No. 61/473,256 entitled Optical System and Method of Use, which is incorporated by reference in its entirety.

FIG. 13 is a schematic diagram of a side view of a system 3300 for detecting spectral and spatial information in a continuous flow PCR system, in accordance with various embodiments. System 3300 includes laser 3310, line generator 3320, tube array 3330, imaging lens 3340, spectrograph 3350, and imager 3360. Laser 3310 emits incident beam of electromagnetic radiation 3311.

Line generator 3320 receives incident beam 3311 from laser 3310. Line generator 3320 transforms incident beam 3311 into incident line of electromagnetic radiation 3321.

On other words, line generator 3320 converts the power distribution of incident beam 3311 from a non-uniform distribution to a uniform distribution. Line generator 3320 is a Powell lens, for example. In various embodiments, line generator 3320 is a diffractive line generator.

Tube array 3330 receives incident line 3321 from line generator 3320. Tube array 3330 includes one or more transparent tubes in fluid communication with one or more micro-channels of a PCR system. In various embodiments, one or more optical elements 3322 are placed between line generator 3320 and tube array 3320 to steer incident line 3321 from line generator 3320 to tube array 3330. As shown in FIG. 13, one or more optical elements 3322 allow system 3300 to be package in an overall smaller volume, for example. In various embodiments, mirror 3325 is also placed between line generator 3320 and tube array 3330 to steer incident line 3321 from line generator 3320 to tube array 3330. Mirror 3325 allows tube array 3330 to be positioned horizontally in system 3300, for example.

Imaging lens 3340 receives reflected electromagnetic radiation 3331 from tube array 3330 and focuses reflected electromagnetic radiation 3331. In various embodiments, one or more optical elements (not shown) are placed between tube array 3330 and imaging lens 3340 to steer reflected electromagnetic radiation 3331 from tube array 3330 to imaging lens 3340. In various embodiments, mirror 3325 is placed between tube array 3330 and imaging lens 3340 to steer reflected electromagnetic radiation 3331 from tube array 3330 to imaging lens 3340. Imaging lens 3340 is a wide-iris lens with a variable aperture, for example. In various embodiments, imaging lens 3340 includes one or more optical filters (not shown). The one or more optical filters remove reflection of incident line 3321 from reflected electromagnetic radiation 3331, for example.

Spectrograph 3350 receives the focused reflected electromagnetic radiation (not shown) from the imaging lens 3340. Spectrograph 3350 detects a spectral intensity from the focused reflected electromagnetic radiation. Spectrograph 3350 can detect spectral wavelengths between 400 and 800 nanometers, for example.

Imager 3360 receives the focused reflected electromagnetic radiation from imaging lens 3340. Imager 3360 detects a location of the spectral intensity. Imager 3360 is a CCD camera, for example.

In various embodiments, system 3300 also includes a processor (not shown). The processor receives the spectral intensity from spectrograph 3350 and receives the location from imager 3360. The processor determines an intensity value for a sample moving through tube array 3330 from the spectral intensity and the location.

Software

Figure 14:
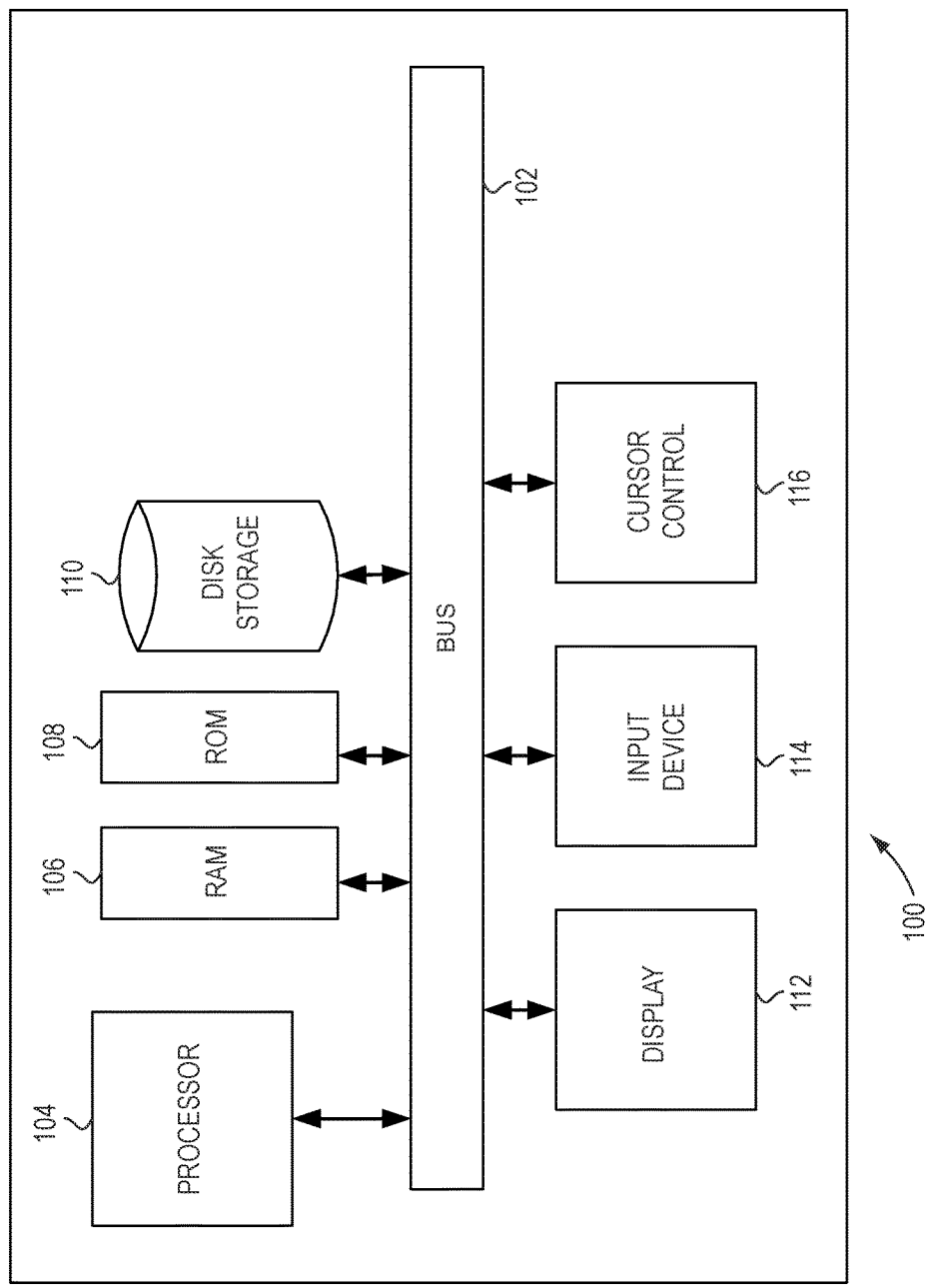
FIG. 14 is a block diagram that illustrates a computer system.

FIG. 14 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for determining base calls, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Referring to FIG. 6 is a schematic diagram showing a system 200 for high throughput PCR amplification and analysis, in accordance with various embodiments. System 200 includes PCR system 210 and processor 220. PCR system 210, in turn, includes liquid handling system 230, fluid pumping system 240, post-bridge detection system 250, thermocycler 260, and endpoint detection system 270.

Processor 220 is in communication with PCR system 210. Processor 220 can include, but is not limited to, a computer, a microprocessor, a microcontroller, an application specific integrated circuit (ASIC), or any device capable of executing instructions and sending and receiving data or control communications.

Processor 220 instructs liquid handling system 230 to obtain a plurality of samples and a plurality of reagents for a PCR experiment. In various embodiments, processor 220 instructs liquid handling system 230 to pipette samples from a first sample support device (not shown) located on tray 231 of liquid handling system 230, pipette assay reagents from a second sample support device (not shown) located on tray 232 of liquid handling system 230, and pipette a master mix reagent from vessel 233.

Processor 220 instructs fluid pumping system 240 to maintain a continuous flow of a transport fluid through a plurality of micro-channels. The transport fluid or oil is a passive buffer for carrying samples around system 200. FIG. 6 shows a single micro-channel of the plurality of micro-channels. This single micro-channel or tube includes draft line 241 and thermocycler line 242. Draft line 241 is used to bleed off excess transport fluid and maintain the continuous flow of a transport fluid through the micro-channel at a constant flow rate. Thermocycler line 242 is used to carry mixed samples through system 200.

Processor 220 instructs fluid pumping system 240 to maintain a continuous flow of a transport fluid in order to receive the plurality of samples and the plurality of reagents from liquid handling system 230 as droplets in the plurality of micro-channels. The continuous flow of a transport fluid by fluid pumping system 240 draws a sample droplet from tip 235 of liquid handling system 230 up through line 245 of fluid pumping system 240. Similarly, the continuous flow of a transport fluid by fluid pumping system 240 draws an assay reagent droplet from tip 236 of liquid handling system 230 up through line 246 of fluid pumping system 240 and draws a master mix reagent droplet from tip 237 of liquid handling system 230 up through line 247 of fluid pumping system 240, for example.

Junction 249 is an exemplary liquid bridge for mixing samples and reagents for a single micro-channel. Lines 245, 246, and 247 meet at junction 249. Through precise timing control, processor 220 instructs liquid handling system 230 to select sample, assay reagent, and master mix droplets using tips 235, 236, and 247 at specific times so that fluid pumping system 240 draws these droplets to junction 249 at the same time. Because sample, assay reagent, and master mix droplets reach junction 249 simultaneously, they are mixed as they are moving with the continuous flow of transport fluid. The mixture produces a mixed sample droplet. This mixed sample droplet leaves junction 249 and enters thermocycler line 242. The mixed sample droplet continues moving with the continuous flow of transport fluid at a constant flow rate in thermocycler line 242.

In order to determine if each mixed sample droplet is mixed correctly, processor 220 receives one or more post-bridge detection values for each mixed sample droplet of the plurality of mixed sample droplets from post-bridge detection system 250. Post-bridge detection system 250, for example, detects mixed sample droplets in thermocycler line 242 at precise time steps selected by processor 220. In various embodiments, post-bridge detection system 250 is an optical system that includes one or more sources of illumination and one or more cameras. In various embodiments, one camera is used and the one or more post-bridge detection values include the intensity of electromagnetic radiation absorbed or reflected by each mixed sample droplet.

In various embodiments, three cameras are used by post-bridge detection system 250. The one or more post-bridge detection values received by processor 220 then include a first intensity of electromagnetic radiation emitted by a first dye of a sample of each mixed sample droplet, a second intensity of electromagnetic radiation emitted by a second dye of an assay reagent of each mixed sample droplet, and a third intensity of electromagnetic radiation emitted by a third dye of a master mix reagent of the mixed sample droplet. In various embodiments, the one or more post-bridge detection values also include a time stamp of the mixed sample droplet so the processor can identify the sample and reagents used to create the mixed sample droplet.

In various embodiments, processor 220 instructs liquid handling system 230 to re-sample a sample and an assay reagent of a mixed sample droplet, if processor 220 determines from the one or more post-bridge detection values that the mixed sample droplet is mixed incorrectly. In other words, if processor 220 determines that the one or more post-bridge detection values that the mixed sample droplet are not indicative of a proper mixture, processor instructs liquid handling system 230 to re-sample the sample and reagents used to create the mixed sample droplet.

Finally, processor 220 receives from endpoint detection system 270 one or more endpoint detection values for each mixed sample droplet of the plurality of mixed sample droplets. Processor 220 uses the one or more endpoint detection values to analyze the PCR experiment. In various embodiments, endpoint detection system 270 is also an optical detection system. Endpoint detection system 270 is a hyperspectral imaging system that determines both spatial and spectral information, for example. Therefore, in various embodiments, the one or more endpoint detection values include the location of a micro-channel and a spectral intensity value detected from that micro-channel. The location of the micro-channel allows processor 220 to identify the mixed sample droplet and the spectral intensity value detected provides a measure of the result of the PCR experiment.

Figure 15:
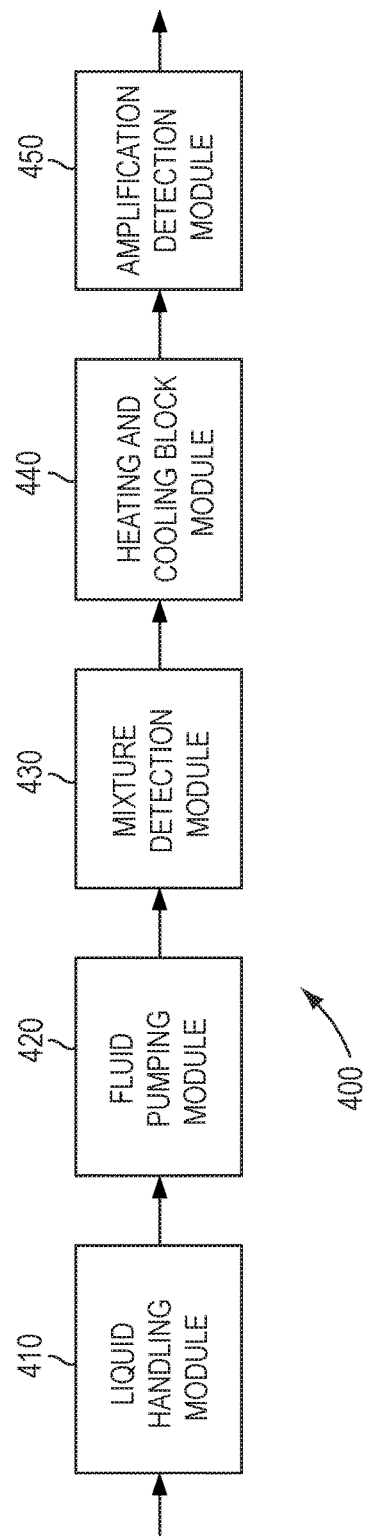
FIG. 15 is a schematic diagram of a system that includes one or more distinct software modules that perform a method for high throughput PCR amplification and analysis.

FIG. 15 is a schematic diagram of a system 400 that includes one or more distinct software modules that perform a method for high throughput PCR amplification and analysis, in accordance with various embodiments. System 400 includes liquid handling module 410, fluid pumping module 420, post-bridge detection module 430, thermocycler module 440, and endpoint detection module 450.

In order to enable system operation the following software controlled elements are present: fluid pumping system, liquid handling/plate handling system, post-bridge detection, thermocycler, endpoint detection, and ancillary equipment. The fluid pumping system includes five flow sensors, five pumps and more than 40 level sensors and valves. The liquid handling/plate handling system includes a plate stacker, a barcode reader, and a 15 axis sampling unit. The post-bridge detection includes three Basler cameras. The thermocycler includes four 24-line temperature controlled thermocyclers (TCs) each with separate denaturation blocks. The endpoint detection includes one Hamamatsu Orca camera and one laser.

In order to enable the system operation the following software controlled elements are present:
Fluid Pumping System
   a. 5× Flow Sensors
   b. 5× Pumps
   c. 40+ Level Sensors and Valves
Liquid Handling/Plate Handling System
   a. OEM Plate Stacker
   b. Barcode Reader
   c. 15 axis sampling unit
Post-bridge Detection
   a. 1× Basler Cameras
Thermocycler
   a. 4 24-line temperature controlled TCs each with separate denaturation block
Endpoint Detection
   a. 1× Hamamatsu Orca Camera
   b. 1× Laser
Ancillary Equipment
   a. LT00399 entitled High-throughput qPCR Control and Analysis System, filed December XX, 2010, and which is incorporated by reference in its entirety.

In some embodiments, the system may be controlled using two different ASCII .csv files. The command file will be titled in the format BARCODETRAY1_BARCODETRAY2_cmds.csv while the volume file will be titled BARCODETRAY1_vols.csv. The command file contains a list of well combinations which will be sampled by the instrument. The volume file contains information pertaining to the contents (volume and components) of each well on the plate. On receiving a RUN command the instrument will read the barcodes of each plate present. It will search for matching command and volume files and if present will process this project. Results will be outputted in the form BARCODETRAY1_BARCODETRAY2_rslts.csv.

In FIG. 15 waypoints P1 through to P6 are shown. Both trays T1 and T2 can access all 6 waypoints. In our current iteration P1 and P6 not used, P2 is used for barcode reading, P3 for upstack/downstack into Hotel 1 on the plate-changer, P4 the same for Hotel 2 and P5 will be used by Monsanto robots to load and unload plates.

Graphical User Interface (GUI)

In some embodiments the system may provide for interaction between the GUI and the instrument. In some embodiments, the interaction includes commands to control the plate stacker and also the transfer of files. In some embodiments, to transfer files an FTP setup is used. There is an FTP server that stores files and waits for clients to connect to it. The GUI acts as a client to connect to the FTP server and transfer files. The instrument can also connect to the same FTP server and transfer files. To control the plate stacker a custom TCP interface is used. The instrument acts as a server and waits for the GUI to connect to it. After a connection is established predefined TCP commands may be sent and received to control the instrument.

FTP

Figure 16:
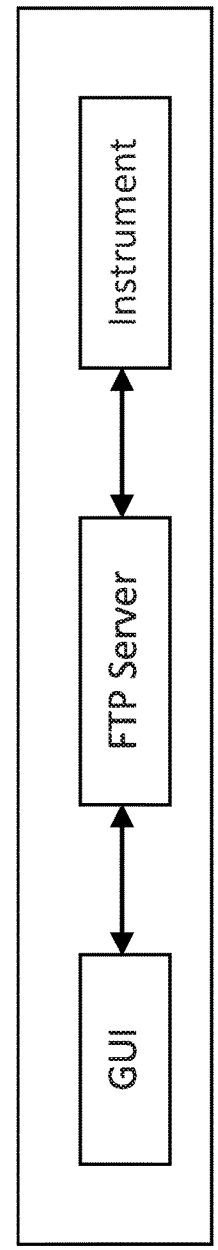
FIG. 16 is a schematic diagram showing how files are transferred between a graphical user interface (GUI) and an instrument, in accordance with various embodiments.

Command files and volume files can be created and modified using the GUI. These files can then be transferred to the instrument. The files are transferred using an FTP server. This process is illustrated in FIG. 16. FIG. 16 is a schematic diagram showing how files are transferred between a graphical user interface (GUI) and an instrument, in accordance with various embodiments. Command files and volume files can be created and modified using the GUI. These files can then be transferred to the instrument. The files are transferred using an FTP server.

Figure 17:
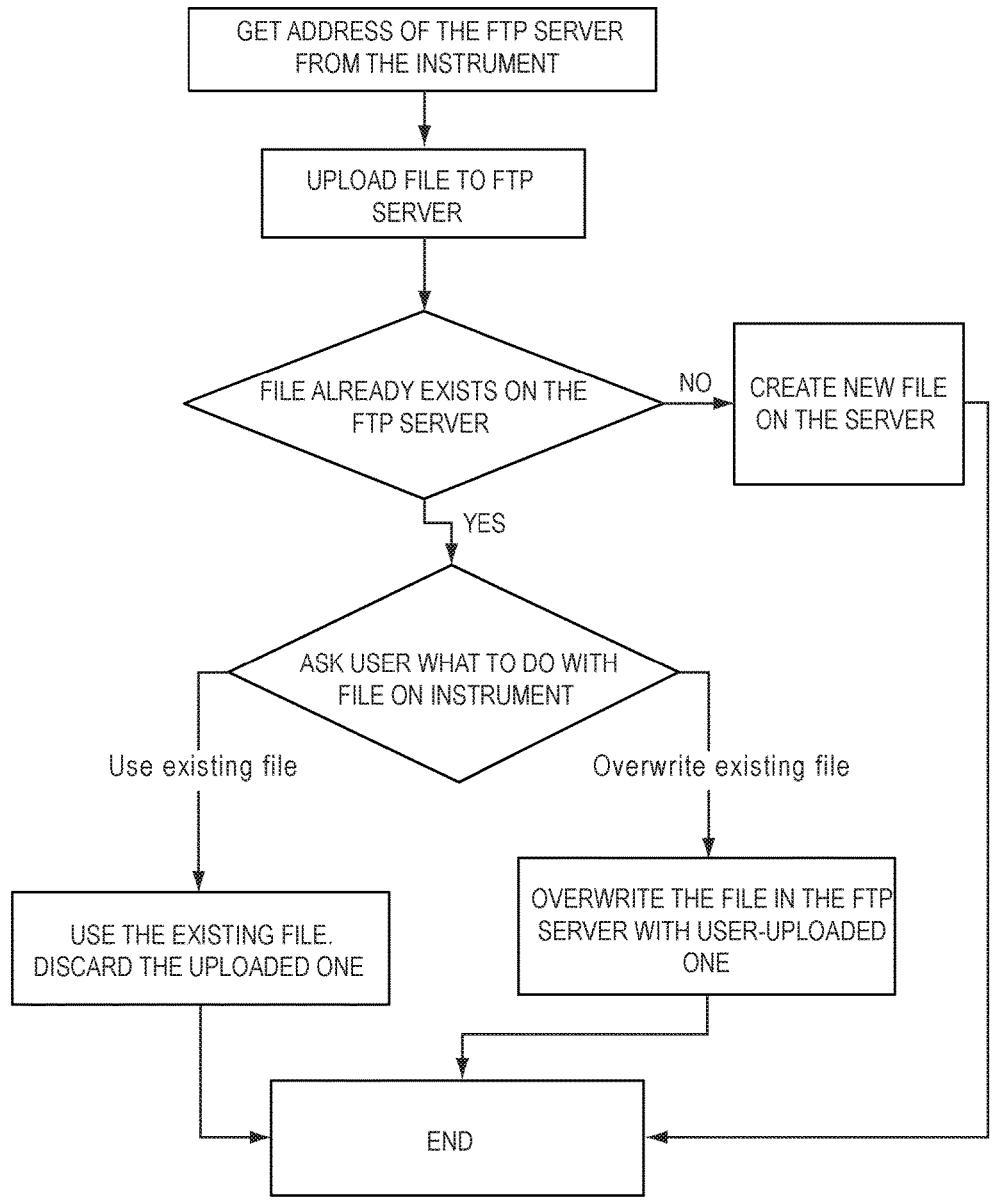
FIG. 17 is a flowchart showing a method for uploading a file using a file transfer protocol (FTP) server, in accordance with various embodiments.

FIG. 17 is a flowchart showing a method for uploading a file using a file transfer protocol (FTP) server, in accordance with various embodiments. To upload a file, the GUI sends a TCP command to the instrument asking it for the address of the FTP server. Once the instrument has responded with this information, the GUI connects to the instrument and uploads a file. If the file already exists on the FTP server the user is asked if they want to keep it or overwrite it.

To download a file, the GUI sends a TCP command to the instrument asking it for the address of the FTP server. Once the instrument has responded with this information, the GUI connects to the instrument and presents a list of files available for downloading. The user selects a file, and the GUI then downloads it to a predefined location on the local computer.

To upload a file the GUI sends a TCP command to the instrument asking it for the address of the FTP server. Once the instrument has responded with this information the GUI connects to the instrument and uploads a file. If the file already exists on the FTP server the user is asked if they want to keep it or overwrite it.

To download a file the GUI sends a TCP command to the instrument asking it for the address of the FTP server. Once the instrument has responded with this information the GUI connects to the instrument and presents a list of files available for downloading. The user selects a file and the GUI then downloads it to a predefined location on the local computer.

Plate Changing

The plate stacker allows the user of the instrument to load multiple plates at once and run them without having to explicitly load and run each plate combination individually. The stacker is divided into two compartments. Each compartment is loaded with plates. At run time the user tells the GUI which combinations to run. The GUI doesn't know which plates are in the stacker. Through a series of TCP commands instructing the instrument to transfer plates between the stacker and the instrument proper, and barcode the plates, the GUI can instruct the instrument to run all the selected combinations.

The optics of the system is such that the system can simultaneously measure from 96 channels. A suitable embodiment of the optical system may be found in U.S. patent application Ser. No. 61/473,263 entitled "High-throughput qPCR Control and Analysis System", which is incorporated by reference in its entirety.

Further provided herein is a method for detecting proper mixing of at least three liquids, comprising mixing together a first liquid, a second liquid, and a third liquid, each being miscible with the others, to form a mixed sample droplet, the first liquid comprising a first fluorescent dye, the second liquid comprising a second fluorescent dye, and the third liquid comprising a third fluorescent dye, each of the first, second, and third fluorescent dyes emitting fluorescence upon excitation wherein the fluorescence emitted from each is spectrally resolvable from the fluorescence emitted from the others, moving the mixed sample droplet in a conduit, irradiating the mixed sample droplet in the conduit with an excitation source; and detecting emissions from the mixed sample droplet to determine whether each of the first, second, and third fluorescent dyes is present in the mixed sample droplet.

Provided herein is a method for detecting a droplet in system comprising moving the mixed sample droplet in a conduit; irradiating the mixed sample droplet in the conduit with an excitation source; and detecting emissions from the mixed sample droplet to determine whether each of the first, second, and third fluorescent dyes is present in the mixed sample droplet. In some embodiments of the method, the first liquid comprises a first droplet, the first droplet is encompassed by a carrier fluid that is substantially immiscible with the first liquid, the second liquid comprises a second droplet, the second droplet is encompassed by the carrier fluid, the third liquid comprises a third droplet, and the third droplet is encompassed by the carrier fluid. The mixed sample droplet may be encompassed by a carrier fluid that is substantially immiscible with the mixed sample droplet. The mixed sample droplet may be formed at an intersection of the conduit with three other conduits, each of the other conduits containing therein the first liquid, the second liquid, and the third liquid, respectively. The excitation source may include one or more LEDs. The excitation source comprises one or more blue LEDs, each blue LED emitting an excitation beam having a single wavelength that excites each of the first, second, and third fluorescent dyes. The detecting comprises detecting emission from the first fluorescent dye using a first detector, detecting emission from the second fluorescent dye using a second detector, and detecting emission from the third fluorescent dye using a third detector. In some embodiments, the method may further comprise tracking the mixed sample droplet as it moves in the conduit and accepting or rejecting data generated by downstream processing of the mixed sample droplet based on the emissions detected. Additionally, the method may further comprising forming a train of droplets including the mixed sample droplet and detecting emissions from each droplet of the train of droplets. In some embodiments, the method may further comprising forming a train of droplets including the mixed sample droplet, the train of droplets comprising carriages each comprising a plurality of spaced apart droplets, wherein a first spacing is provided between adjacent droplets within each carriage, and the carriages are spaced apart from adjacent carriages by a second spacing that differs from the first spacing. Additionally the methods provided herein may include determining, based on the detected emissions, that proper mixing of the first liquid, second liquid, and third liquid has occurred in the mixed sample droplet; and gathering data from downstream processing of the mixed sample droplet. Alternatively, the method may comprise determining, based on the detected emissions, that improper mixing of the first liquid, second, liquid, and third liquid has occurred in the mixed sample droplet; and recording occurrence of an error; forming a new mixed sample droplet from the first liquid, the second liquid, and the third liquid; and ignoring data generated by downstream processing of the mixed sample droplet. In some embodiments, the first and second dyes comprise a passive reference dye and the third dye comprises a reporter dye.

EXAMPLES

Example 1

In some embodiments of the system, an alternative approach to post-bridge diagnostic detection may occur. In such an embodiment of an alternative approach for the post bridge error correction a single camera is used and the droplet time peak width (corresponding to droplet length) is detected. Using the droplet peak width approach and incorporating a +/−7% tolerance, erroneous droplet carriages can be identified. Carriages of 9 droplets (3 reactions in triplicate) were used.

A droplet count check is used to pass or fail a carriage. Then standard deviation of the 9 droplet carriage is then calculated. If the standard deviation is above a set threshold based on a set tolerance, then the carriage is rejected. The results of which are presented in Tables 1, 2, and 3.

TABLE 1

| Droplet Types | Weighting (droplet length/time) |
|---|---|
| Standard Droplet | 10 |
| MasterMix & Sample (MM&GA) | 8.5 |
| MasterMix | 7 |
| Sample/Gene Assay (GA) | 1.5 |

Note:
Weighting is based on the percentage size of the droplet from initial viewing of video evidence.

TABLE 2

| Main Failure Events | Premixing 1 | Droplet 1 | Sample & | 3 | This case will |
| | | Droplet 2 | GA MM | 7 | cause a droplet error count |
| | No Mixing | Droplet 1 | Sample | 1.5 | This case will |
| | | Droplet 2 | GA | 1.5 | cause a droplet |
| | | Droplet 3 | MM | 7 | count error |
| | Droplet Splitting (rare) | | | | This case will cause a droplet count error |
| | Premixing 2 | Droplet 1 | Sample (or | 8.5 | This case will |
| | | Droplet 2 | GA) & MM Standard Droplet & Sample | 11.5 | not cause error |

TABLE 3

| Droplet # | Perfect Carriage | Allow a tolerance of +/−5% | Allow a tolerance of +/−7% | Premixing 2 | Premixing 1 (Droplet Count & Width) | Allow a tolerance of +/−10% |
|---|---|---|---|---|---|---|
| 1 | 10 | 10.5 | 10.7 | 10 | 3 | 10 |
| 2 | 10 | 10.5 | 10.7 | 10 | 7 | 9 |
| 3 | 10 | 10.5 | 10.7 | 10 | 10 | 11 |
| 4 | 10 | 9.5 | 9.3 | 8.5 | 10 | 9 |
| 5 | 10 | 9.5 | 9.3 | 11.5 | 10 | 10 |
| 6 | 10 | 10.5 | 10.7 | 10 | 10 | 11 |
| 7 | 10 | 9.5 | 9.3 | 10 | 10 | 9 |
| 8 | 10 | 9.5 | 9.3 | 10 | 10 | 10 |
| 9 | 10 | 10.5 | 10.7 | 10 | 10 | 11 |
| | | | | | 10 | |
| Standard Deviation | 0 | 0.527046277 | 0.737864787 | 0.75 | 2.309401077 | 0.866025404 |
| | Pass | Pass | Pass | Fail | Fail | Fail |

Example 2

Schematic of One Embodiment of the System

Figure 18:
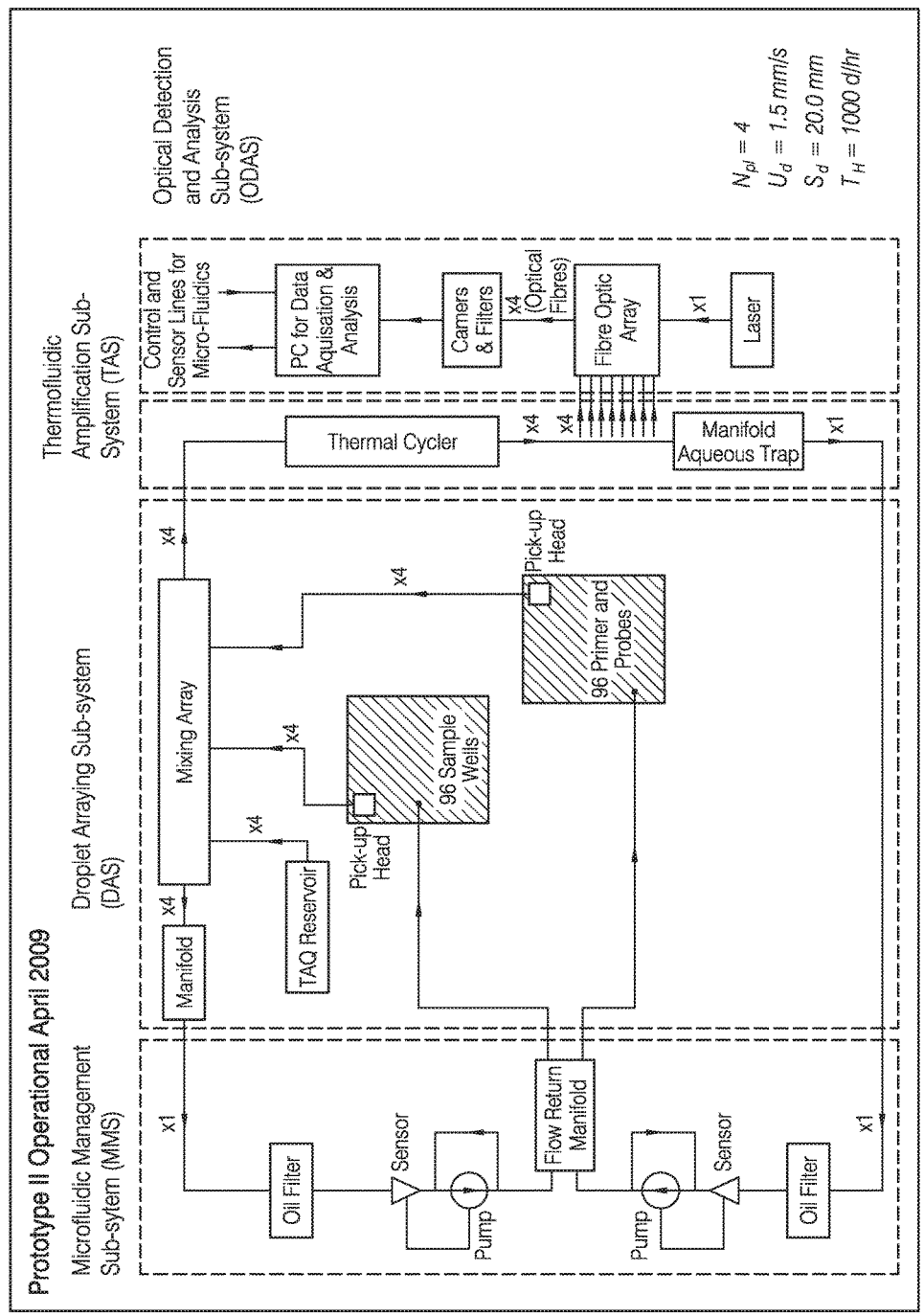
FIG. 18 is a schematic of one embodiment of the system.

FIG. 18 shows one embodiment of a schematic of the system described herein.

Graphical User Interface Module:

This part of the program is seen by the user to access the machine and all components of the program. The layout of the GUI module will be dictated by the functionality of the main program:

From SB:

Is machine setup required before each run? Or intermittently?

Is image calibration required before each run? Or intermittently?

From Monsanto:

Does the machine need to have random access—well by well access—or will the machine access entire plates for every run?

Should results be plotted on screen or generated in the background?

What format are Monsanto databases in? What information from the databases should be passed through the program to the Report Generation step?

Image Calibration Module/Intensity Data Module

These modules will be based on existing Matlab code. They are used to take fluorescent intensity data from the cameras and format it into a series of numerical values suitable for data analysis.

Technology:

Imaging Source Cameras or alternatives:

Driver Compatibility

Method of Detection

Fibres or alternatives (e.g. Current Digital Setup)

Three Cameras

Endpoint only or Entry/Exit Measurements

Other Issues?

System Controls Module (Command List/Stage Movements)

This section of the program will control the flow rates with the platform, and will also control the positioning stages in order to generate a series of mixed droplets in the correct order.

Pumps/Sensors:

Will the system run using 8 (or 12) HNP Pump or Sensor Combinations:

Thermocycler Line

Primary Draft Line

TAQ Draft Line

Alternative Architecture

Alternative Components

Large Pump with Flow Control Valves

Stages

Equipment:

Standa Stages

Alternative Stages
  More Expensive
  More Robust
  Faster
  Require Drivers
Dip Heights
  High-speed dipping
  Incremental dipping
  Sensor measuring interface
  Secondary Dipping/Wrapped Tip
  Interdependence of flow-rates and dip-times. Lock in flow-rates.
Method
  Analysis in duplicate/triplicate
  Location of NTCs
  How will droplets be identified
  Carriage Spacing
  Spiked Droplets
    Effect stage movements
  Data Analysis Module
  This module will be based on existing Matlab code. The module will take in intensity and time data which has been formatted correctly. It will analyse this data looking for discrete droplets. These droplets will then be associated with a PRIMER/SAMPLE pair which is also loaded into the program. The intensities of FAM/VIC will then be calculated and reports generated in the correct format. Errors in carriages (too many/too few droplets) will be reported
    Measurement Locations
    After Mixer
    Cycle 7
    Cycle 42
    Data-stream form
    Trains/Carriages using spacing
    Trains/Carriages using spiked drops
    Method of Data Analyse
    Endpoint Intensities
    Normalise using ROX
    Normalise using ROX and Cycle 7
    Format for report generation
    VIC vs. FAM plots
    Table of Boolean Data
    Exception Handling
  Report Generation Module
  This module outputs formatted data both to files and to the GUI.
    Format of the output files/data
    What is recorded—what is discarded
    Compatible with the Monsanto Database
    Exception Reports
    Exception Handling
  This module is used as a link between the data-analysis module and the stage control module. It will also monitor the performance of the physical components of the system and take appropriate action.
    Droplet Stream Error
    Not enough droplets per carriage
      Action e.g. Repeat Carriage and Log
      Action e.g. Increment dipping tip down
    Too many droplets per carriage
      Action e.g. Repeat Carriage and Log
      Action e.g. Reduce Primer Dip time
    No droplets detected
      Action e.g. Abort Run
    Other possible errors
    Component Error
    Stage Motion not detected
    Flow rates outside tolerances
    Flow sensor noise-free
  Overall System Architecture:
  The system will be required to run off one PC. Architecture must permit components to reach this PC and be connected to it. In a lab environment it would be advantages to have as few exposed cables as possible linking the PC to the platform.
    List of Components:
    Powerful PC for Data Analysis and Report Generation
    Sufficient Ports/Connectors to handle all components:
      Example:
        3× Firewire Cameras
        8× RS-232 for 8 sensors
        1× RS-232 for 8 pumps
        2×USB for 6 stages While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for detecting a mixed droplet, the system comprising:
    a fluid charging apparatus configured to generate an electric field sufficient to induce a net charge in a liquid received in the fluid charging apparatus;
    a microfluidics network in fluid communication with the fluid charging apparatus, the microfluidics network comprising:
        a first liquid input configured to receive from the fluid charging apparatus a a first liquid induced with a net charge, the first liquid input configured to flow the first liquid;
        a second liquid input configured to flow a second liquid; and
        a mixer in fluid communication with the first liquid input to receive the first liquid induced with the net charge, and with the second liquid input to receive the second liquid, wherein the mixer is configured to segment the first liquid induced with the net charge into at least one first charged liquid droplet and to segment the second liquid into at least one second liquid droplet and to create a mixed droplet from the first charged liquid droplet and the second liquid droplet; and
    a detector positioned downstream of the mixer, wherein the detector is configured to detect the mixed droplet in a flow path downstream from the mixer.

2. The system of claim 1, further comprising a third liquid input configured to provide a third liquid, the third liquid input in fluid communication with the mixer, wherein the mixer is configured to receive and to segment the third liquid into at least one third liquid droplet.

3. The system of claim 2, wherein the mixer mixes the first charged liquid droplet, the second liquid droplet, and the third liquid droplet to form the mixed droplet.

4. The system of claim 3, wherein the detector is configured to detect a first wavelength corresponding to emission from a first fluorescent dye in the mixed droplet, a second wavelength corresponding to emission from a second fluorescent dye in the mixed droplet, and a third wavelength corresponding to emission from a third fluorescent dye in the mixed droplet.

5. The system of claim 1, wherein the system further comprises a thermocycler.

6. The system of claim 1, wherein the fluid charging apparatus is a static charge bar.

7. The system of claim 6, wherein the static charge bar comprises an electrode.

8. The system of claim 1, wherein the fluid charging apparatus comprises:
an ionizing electrode;
a ground electrode; and
a fluid vessel positioned between the ionizing electrode and the ground electrode, the fluid vessel defining a reservoir configured to hold liquid within an electric field upon a condition of the electric field being generated by the ionizing and ground electrodes.

9. The system of claim 8, wherein the ionizing electrode comprises an emitter plate and one or more emitter pins connected to the emitter plate.

10. The system of claim 8, wherein:
the ionizing electrode is cruciform;
the fluid vessel has a perimeter; and
the ground electrode has a perimeter substantially matching the perimeter of the fluid vessel.

11. The system of claim 8, wherein the ionizing electrode and ground electrode are operable to generate an ion field having a positive polarity and a positive net charge.

12. The system of claim 8, wherein the ionizing electrode and ground electrode are operable to generate an ion field having a negative polarity and a negative net charge.

13. The system of claim 8, further comprising a fluid sampling device in fluid communication to withdraw liquid from the fluid vessel and to deliver liquid withdrawn from the fluid vessel to at least one of the first and second liquid inputs.

14. The system of claim 1, wherein the fluid charging apparatus comprises a static generator configured to generate static electricity sufficient to induce a static charge on at least one component of the fluid charging apparatus.

15. The system of claim 1, wherein the mixer is configured to preserve a net charge on liquid received from the fluid charging apparatus until at least creation of the mixed droplet.

16. The system of claim 1, wherein the detector is configured to detect in the mixed droplet both a first liquid characteristic associated with the first charged liquid and a second liquid characteristic associated with the second liquid.

17. The system of claim 16, wherein the first liquid characteristic is a first wavelength, the second liquid characteristic is a second wavelength, and the detector is configured to detect the first and second wavelengths.

18. The system of claim 1, wherein the detector comprises a first detector configured to detect in the mixed droplet a first liquid characteristic associated with the first charged liquid and a second detector configured to detect in the mixed droplet a second liquid characteristic associated with the second liquid.

* * * * *